(12) United States Patent
Koizumi et al.

(10) Patent No.: US 11,382,904 B2
(45) Date of Patent: Jul. 12, 2022

(54) THERAPEUTIC DRUG FOR DISEASES RELATED TO ENDOPLASMIC RETICULUM CELL DEATH IN CORNEAL ENDOTHELIUM

(71) Applicants: KYOTO PREFECTURAL PUBLIC UNIVERSITY CORPORATION, Kyoto (JP); THE DOSHISHA, Kyoto (JP); SENJU PHARMACEUTICAL CO., LTD., Osaka (JP)

(72) Inventors: Noriko Koizumi, Kyotanabe (JP); Naoki Okumura, Kyotanabe (JP); Shigeru Kinoshita, Kyoto (JP)

(73) Assignees: Kyoto Prefectural Public University Corporation, Kyoto (JP); The Doshisha, Kyoto (JP); Senju Pharmaceutical Co., Ltd., Osaka (JP)

( * ) Notice: Subject to any disclaimer, the term of this patent is extended or adjusted under 35 U.S.C. 154(b) by 0 days.

(21) Appl. No.: 15/031,183

(22) PCT Filed: Oct. 30, 2014

(86) PCT No.: PCT/JP2014/079513
§ 371 (c)(1),
(2) Date: Apr. 21, 2016

(87) PCT Pub. No.: WO2015/064768
PCT Pub. Date: May 7, 2015

(65) Prior Publication Data
US 2016/0296505 A1    Oct. 13, 2016

(30) Foreign Application Priority Data

Oct. 31, 2013 (JP) .............................. JP2013-227048
Sep. 10, 2014 (JP) .............................. JP2014-184172

(51) Int. Cl.
| | | |
|---|---|---|
| A61K 31/4439 | (2006.01) | |
| A61K 31/444 | (2006.01) | |
| A61K 31/4709 | (2006.01) | |
| A61K 9/00 | (2006.01) | |
| A61K 31/713 | (2006.01) | |
| A61K 31/519 | (2006.01) | |
| A61K 38/00 | (2006.01) | |
| A61K 31/437 | (2006.01) | |
| A61K 39/395 | (2006.01) | |
| C07K 16/22 | (2006.01) | |

(52) U.S. Cl.
CPC ........ *A61K 31/4439* (2013.01); *A61K 9/0048* (2013.01); *A61K 31/437* (2013.01); *A61K 31/444* (2013.01); *A61K 31/4709* (2013.01); *A61K 31/519* (2013.01); *A61K 31/713* (2013.01); *A61K 38/00* (2013.01); *A61K 39/3955* (2013.01); *C07K 16/22* (2013.01)

(58) Field of Classification Search
None
See application file for complete search history.

(56) References Cited

U.S. PATENT DOCUMENTS

| | | | |
|---|---|---|---|
| 5,703,047 A | 12/1997 | Wilson | |
| 2002/0115589 A1* | 8/2002 | Nixon | A61K 38/57 514/8.9 |
| 2003/0191137 A1 | 10/2003 | Kim et al. | |
| 2004/0038856 A1 | 2/2004 | Chakravarty et al. | |
| 2007/0014767 A1 | 1/2007 | Ezquerro Saenz et al. | |
| 2007/0142376 A1* | 6/2007 | Fleenor | A61K 31/444 514/235.2 |
| 2008/0194531 A1* | 8/2008 | Steer | A61K 31/575 514/182 |
| 2008/0267946 A1 | 10/2008 | Kim et al. | |
| 2009/0062247 A1 | 3/2009 | Huang et al. | |
| 2010/0087486 A1* | 4/2010 | Nakamura | A61K 31/4709 514/333 |
| 2010/0222280 A1 | 9/2010 | Dotor Herrerías et al. | |
| 2010/0267731 A1 | 10/2010 | Nakamura | |
| 2012/0315256 A1 | 12/2012 | Dotor De Las Herrerias et al. | |
| 2015/0044178 A1 | 2/2015 | Kinoshita et al. | |

(Continued)

FOREIGN PATENT DOCUMENTS

| | | |
|---|---|---|
| JP | 2008-513465 A | 5/2008 |
| JP | 2008-533000 A | 8/2008 |
| JP | 2012-067097 A | 4/2012 |

(Continued)

OTHER PUBLICATIONS

Ueda et al., Protective effects of TGF-beta inhibitors on retinal blood vessels in the injured rat retina, 2011, J. Pharmacol. Sci., vol. 115, Suppl. 1, Abstract 262P.*
Laping et al. Molecular Pharmacology 2002, vol. 62, No. 1, 58. (Year: 2002).*
Elhalis Ocul. Surf., 2010, Amin ARVO Abstract, Jun. 2013 (Year: 2013).*
Usui IOVS, 1998. (Year: 1998).*
Kim et al., Lithium treatment increases endothelial cell survival and autophagy in a mouse model of Fuchs endothelial corneal dystrophy, The British Journal of Opthalmology (2013), vol. 97:08, p. 1068-1073.
Okumura et al., "Inhibition of TGF-β signaling enables humancorneal endothelial cell expansion in vitro for use in regenerative medicine", Pios One (2013), vol. 08:02, p. e58000.

(Continued)

*Primary Examiner* — Jeffrey S Lundgren
*Assistant Examiner* — Michael J Schmitt
(74) *Attorney, Agent, or Firm* — Leydig, Voit & Mayer, Ltd.

(57) ABSTRACT

The present invention provides a treatment drug or prophylactic drug for diseases, disorders, or conditions related to endoplasmic reticulum (ER) stress. Specifically, the present invention provides a treatment drug or prophylactic drug for diseases, disorders, or conditions related to endoplasmic reticulum (ER) stress in the corneal epithelium, the drug containing a TGFβ-signal inhibitor. As a preferred TGFβ-signal inhibitor, the drug contains 4-[4-(1,3-benzodioxole-5-yl)-5-(2-pyridinyl)-1H-imidazole-2-yl]benzamide.

19 Claims, 12 Drawing Sheets
(6 of 12 Drawing Sheet(s) Filed in Color)

(56) References Cited

U.S. PATENT DOCUMENTS

2016/0158210 A1     6/2016   Koizumi et al.

FOREIGN PATENT DOCUMENTS

| JP | 2013-520405 A | 6/2013 |
|---|---|---|
| JP | 6403217 B2 | 10/2018 |
| RU | 2232771 C2 | 5/2003 |
| WO | WO 2006/031931 A2 | 3/2006 |
| WO | 2006-096011 A1 | 9/2006 |
| WO | WO 2009/146408 A1 | 12/2009 |
| WO | 2011-101478 A1 | 8/2011 |
| WO | WO 2012/009171 A2 | 1/2012 |
| WO | WO 2012/07328 A1 | 6/2012 |
| WO | WO 2013/086236 A2 | 6/2013 |
| WO | 2013-100208 A1 | 7/2013 |
| WO | WO 2015/015654 A1 | 2/2015 |

OTHER PUBLICATIONS

International Search Report in Application No. PCT/JP2014/079513 dated May 7, 2015, (4 pages).
Elhalis et al., "Fuchs Endothelial Corneal Dystrophy," *Ocul. Surf.*, 8(4): 173-184 (2010).
European Patent Office, Extended European Search Report in European Patent Application No. 14857909.7 (dated Jun. 16, 2017).
Mexican Patent Office, Office Action in Mexican Patent Application No. MX/a/2016/001457 (dated Mar. 25, 2019).
Russian Patent Office, Office Action in Russian Patent Application No. 2019107381 (dated Mar. 19, 2019).
Japanese Patent Office, Office Action in Japanese Patent Application No. 2015-545338 (dated Jan. 22, 2019).
European Patent Office, Communication Pursuant to Article 94(3) EPC in European Patent Application No. 14857909.7 (dated Sep. 26, 2018).
Joyce et al., "Proliferative Capacity of Corneal Endothelial Cells," *Exp. Eye Res.*, 95(1): 16-23 (2012).
Motegi et al., "Regulation of bovine corneal endothelial cell cycle by transforming growth factor-β," *Acta Ophthalmol. Scand.*, 81(5): 517-525 (2003).
Russian Patent Office, Official Action in Russian Patent Application No. 2016121150 (dated Aug. 20, 2018).
Russian Patent Office, Search Report in Russian Patent Application No. 2016121150 (dated Jul. 31, 2018).
Mexican Patent Office, Office Action in Mexican Patent Application No. MX/a/2016/005680 (dated May 22, 2019).
Hao et al., "In Vivo Structure Activity Relationship Study of Dorsomorphin Analogs Identifies Selective VEGF and BMP Inhibitors," *ACS Chem. Biol.*, 5(2): 245-253 (2010).
Huang et al., "A Hierarchy of Endothelial Colony-Forming Cell Activity Displayed by Bovine Corneal Endothelial Cells," *Invest. Ophthalmol. Vis. Sci.*, 51(8): 3943-3949 (2010).
Jinnin et al., "Characterization of SIS3, a Novel Specific Inhibitor of Smad3, and Its Effect on Transforming Growth Factor-β1-Induced Extracellular Matrix Expression," *Mol. Pharmacol.*, 69(2): 597-607 (2006).
McCaa, "The Eye and Visual Nervous System: Anatomy, Physiology and Toxicology," *Environ. Health Perspect.*, 44: 1-8 (1982).
Shea, "Distance Learning Course: Anatomy and Physiology of the Eye," *BSM Consulting*, 1-21 (2010-2012).
Smith, "Nutrition and Eye Diseases," *Journal of Orthomolecular Medicine*, 25(2): 67-76 (2010).
Tsukasaki et al., "Nephronectin expression is regulated by SMAD signaling in osteoblast-like MC3T3-E1 cells," *Biochem. Biophys. Res. Commun.*, 425(2): 390-392 (2012).
Uhl et al., "SD-208, a Novel Transforming Growth Factor β Receptor I Kinase Inhibitor, Inhibits Growth and Invasiveness and Enhances Immunogenicity of Murine and Human Glioma Cells In vitro and In vivo," *Cancer Res.*, 64(21): 7954-7961 (2004).
Zhu et al.,"Eye Anatomy," *eLS*, DOI: 10.1002/9780470015902. a0000108.pub2 (John Wiley & Sons, Ltd., Nov. 2012).
Russian Patent Office, Minutes of Interview in Russian Patent Application No. 2016121150 (Aug. 12, 2019).
Yu et al., "Concentration change of TGF-β1 in aqueous humor of rabbits," *Asian Pac. J. Trop. Med.*, 7(3): 241-243 (2014).
Russian Patent Office, Notification on the Results of Invention Patentability Assessment in Russian Patent Application No. 2016121150 (dated Jan. 22, 2019).
Canadian Patent Office, Examination Report in Canadian Patent Application No. 2,919,316 (dated May 7, 2019).
Japanese Patent Office, Official Action in Japanese Patent Application No. 2015-545338 (dated Jul. 17, 2018).
Ashaye et al., "Pattern of Corneal Opacity in Ibadan, Nigeria," *Ann. Afr. Med.*, 3(4): 185-187 (2004).
Wipperman et al., "Evaluation and Management of Corneal Abrasions," *Am. Fam. Physician*, 87(2): 114-120 (2013).
Zou et al., "Keratorefractive surgery and glaucoma," *Int. J. Opthalmol.*, 1(3): 189-194 (2008).
Goodman et al., "Conjunctivitis," *The Journal of the American Medical Association*, 309(20): 2176 (2013).
Amin et al., "Changes in Anterior Corneal Haze with Severity of Fuchs Endothelial Dystrophy," *Invest. Ophthalmol Vis. Sci.*, 54: 1679 (2013).
Ho et al., "Cell Line of Fuchs' Corneal Dystrophy Produces an Abnormal Extracellular Matrix," *The Association for Research in Vision and Ophthalmology*, Abstract for Program No. 1680, Poster Board No. D0315 (Mar. 12, 2013).
Ho et al., "Cell Line of Fuchs' Corneal Dystrophy Produces an Abnormal Extracellular Matrix," *The Association for Research in Vision and Ophthalmology*, Program No. 1680, Poster Board No. D0315 (May 6, 2013).
Koizumi et al., "Development of new therapeutic modalities for corneal endothelial disease focused on the proliferation of corneal endothelial cells using animal models," *Exp. Eye. Res.*, 95(1): 60-67 (2012).
Koizumi, "Development of new therapeutic modalities for corneal endothelial disease using somatic stem cells," *Journal of Clinical and Experimental Medicine*, 241(10): 765-770 (2012).
Okumura et al., "The New Therapeutic Concept of Using a Rho Kinase Inhibitor for the Treatment of Corneal Endothelial Dysfunction," *Cornea*, 30(10): S54-S59 (2011).
Okumura et al., "Activation of TGF-β signaling induces cell death via the unfolded protein response in Fuchs endothelial corneal dystrophy," *Sci. Rep.*, 7(1): 6801 (2017).
Sakamoto et al., "Blockade of TGF-beta by in vivo gene transfer of a soluble TGF-beta type II receptor in the muscle inhibits corneal opacification, edema and angiogenesis," *Gene Therapy*, 7(22):1915-1924 (2000).
Usui et al., "Extracellular Matrix Production Regulation by TGF-β in Corneal Endothelial Cells," *Invest. Ophthalmol. Vis. Sci.*, 39(11): 1981-1989 (1998).
Japanese Patent Office, Official Action in Japanese Patent Application No. 2015-529317 (dated Mar. 14, 2018).
Russian Patent Office, Official Action in Russian Patent Application No. 2016106641 (dated Jun. 20, 2017).
Russian Patent Office, Search Report in Russian Patent Application No. 2016106641 (dated Jun. 20, 2017).
Russian Patent Office, Decision of Refusal in Russian Patent Application No. 2016106641 (dated Aug. 16, 2018).
Brazilian Patent Office, Office Action in Brazilian Patent Application No. BR112016002015-4 (dated Oct. 1, 2019).
Mexican Patent Office, Office Action in Mexican Patent Application No. MX/a/2016/001457 (dated Oct. 17, 2019).
Japanese Patent Office, Office Action in Japanese Patent Application No. 2015-545338 (dated Feb. 4, 2020).
Brazilian Patent Office, Preliminary Office Action in Brazilian Patent Application No. BR112016009493-0 (dated Sep. 24, 2019).
European Patent Office, Communication Pursuant to Article 94(3) EPC in European Patent Application No. 14857909.7 (dated Sep. 3, 2019).
Mexican Patent Office, Office Action in Mexican Patent Application No. MX/a/2016/005680 (dated Sep. 17, 2019).
Eghrari et al., "Fuchs' corneal dystrophy," *Expert. Rev. Ophthalmol.*, 5(2): 147-159 (2010).

(56) References Cited

OTHER PUBLICATIONS

Climo et al., "Comparison of the in-vitro and in-vivo efficacy of FK037, vancomycin, imipenem and nafcillin against staphylococcal species," *J. Antimicrob. Chemother.*, 40(1): 59-66 (1997).

Den Hollander et al., "Comparison of Pharmacodynamics of Azithromycin and Erythromycin In Vitro and In Vivo," *Antimicrob. Agents Chemother.*, 42(2): 377-382 (1998).

Matthaei et al., "Endothelial Cdkn1a (p21) Overexpression and Accelerated Senescence in a Mouse Model of Fuchs Endothelial Corneal Dystrophy," *Invest. Ophthalmol. Vis. Sci.*, 53(10): 6718-6727 (2012).

Rodriguez et al., "In vitro and in vivo comparison of the anti-staphylococcal efficacy of generic products and the innovator of oxacillin," *BMC Infect. Dis.*, 10: 153 (2010).

Wang et al., "The impact of early ADME profiling on drug discovery and development strategy," *Drug Discovery World*, Fall 2004: 73-86 (2004).

Mexican Patent Office, Office Action in Mexican Patent Application No. MX/a/2016/005680 (dated Jul. 13, 2020).

Canadian Patent Office, Examination Report in Canadian Patent Application No. 2,919,316 (dated May 28, 2020).

Canadian Intellectual Property Office, Office Action in Canadian Patent Application No. 2,927,898 (dated Dec. 9, 2020).

Mexican Patent Office, Office Action in Mexican Patent Application No. MX/a/2016/001457 (dated Jul. 13, 2020).

European Patent Office, Extended European Search Report in European Patent Application No. 20195546.5 (dated Mar. 17, 2021).

Japanese Patent Office, Decision of Refusal in Japanese Patent Application No. 2019-197763 (dated Jul. 14, 2021).

Engler et al., "Unfolded protein response in Fuchs Endothelial Corneal Dystrophy: a Unifying Pathogenic Pathway?" *Am. J. Ophthalmol.*, 149(2): 194 (2010).

Park et al., "The chemical chaperone 4-phenylbutyric acid attenuates pressure-overload cardiac hypertrophy by alleviating endoplasmic reticulum stress," *Biochem. Biophys. Res. Commun.*, 421(3): 578-584 (2012).

U.S. Appl. No. 14/907,881, filed Jan. 27, 2016.

Connolly et al., "Complexities of TGF-β Targeted Cancer Therapy," *Int. J. Biol. Sci*, 8(7): 964-978 (2012).

Cui et al., "Selective Inhibition of TGF-β responsive genes by Smad-interacting peptide aptamers from FoxH1, Lef1 and CBP," *Oncogene*, 24: 3864-3874 (2005).

Kang et al., "Combinatorial selection of a single stranded DNA thioaptamer targeting TGF-β1 protein," *Bioorg. Med. Chem. Lett.*, 18: 1835-1839 (2008).

Zhao et al., "Inhibition of Transforming Growth Factor-β1-induced Signaling and Epithelial-to-Mesenchymal Transition by the Smad-binding Peptide Aptamer Trx-SARA," *Mol. Biol. Cell*, 17: 3819-3831 (2006).

Zhu et al., "A Novel Aptamer Targeting TGF-β Receptor II Inhibits Transdifferentiation of Human Tenon's Fibroblasts into Myofibroblast," *Invest. Ophthalmol. Vis. Sci.*, 53: 6897-6903 (2012).

Brazilian National Institute of Industrial Property, Unfavorable Opinion in Braziliation Patent Application No. BR112016002015-4 (dated Apr. 27, 2022).

Russian Federal Service for Intellectual Property, Official Action in Russian Patent Application No. 201907391/04(014267) (dated Mar. 9, 2022).

Russian Federal Service for Intellectual Property, Search Report in Russian Patent Application No. 2019107381/04(014267) (dated Mar. 9, 2022).

\* cited by examiner

Fig. 2
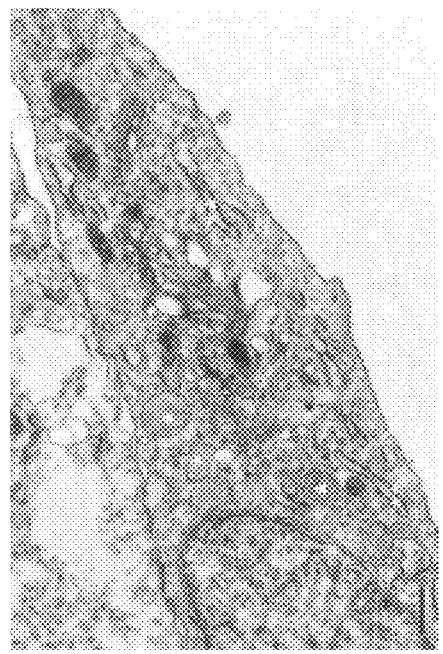 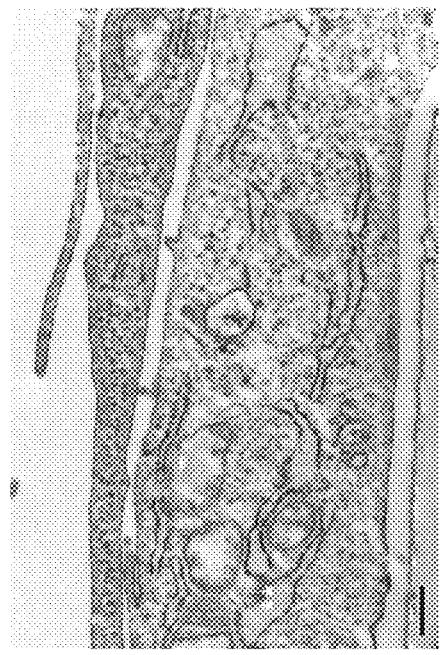
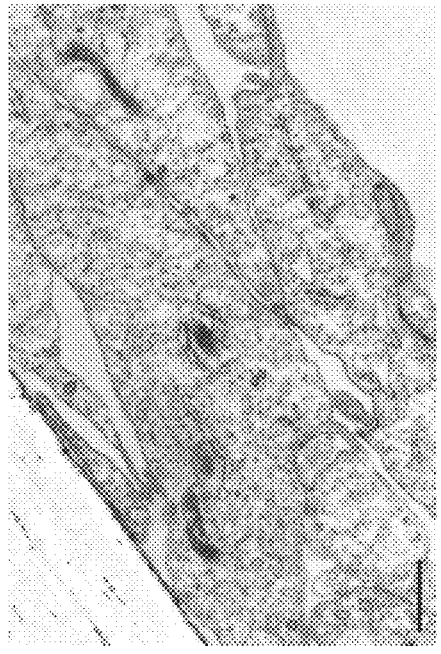 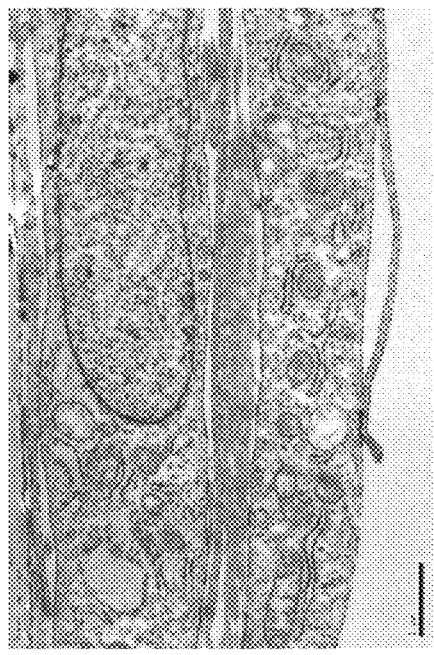
iHCEC iFECD
\* Mitochondria
\*\* Endoplasmic reticulum
\*\*\* Extracellular matrix

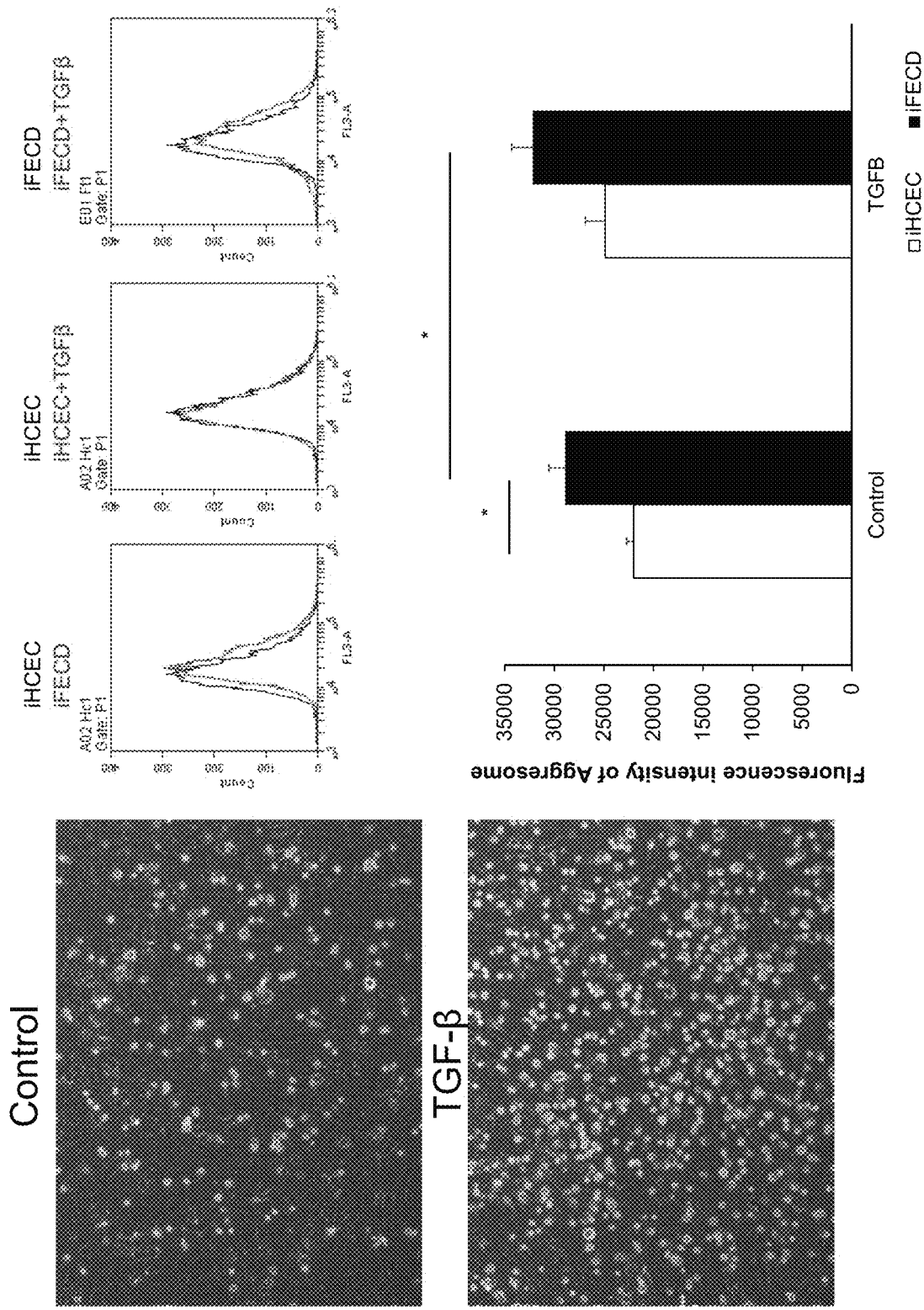

THERAPEUTIC DRUG FOR DISEASES RELATED TO ENDOPLASMIC RETICULUM CELL DEATH IN CORNEAL ENDOTHELIUM

CROSS REFERENCE TO RELATED APPLICATIONS

The present application is the U.S. National Phase of International Patent Application Serial No. PCT/JP2014/079513, filed Oct. 30, 2014, which claims priority to Japanese Patent Application Serial Nos. 2013-227048, filed Oct. 31, 2013 and 2014-184172, filed Sep. 10, 2014. The contents of the foregoing applications are hereby incorporated by reference in their entireties.

TECHNICAL FIELD

The present invention relates to a technique, a method, an agent and the like for treating or preventing a disease, disorder or condition associated with endoplasmic reticulum (ER) related stress and cell death.

BACKGROUND ART

Visual information is recognized when light transmitted into the cornea, which is a transparent tissue at the frontmost part of an eye ball, reaches the retina and excites nerve cells of the retina, and a generated electric signal is transmitted through the optic nerve to the visual cortex of the cerebrum. To attain good vision, it is necessary that the cornea is transparent. The transparency of the cornea is maintained by maintaining constant water content with pumping and barrier functions of corneal endothelial cells.

Human corneal endothelial cells are present at a density of about 3000 cells per 1 $mm^2$ at birth. However, once damaged, human corneal endothelial cells have very limited ability to regenerate.

A research is in progress for diseased conditions of corneal endothelial cells. Non Patent Literature 1 is a document regarding basic research on the relationship between human corneal endothelial cells and oxidative stress. Non Patent Literature 2 is a document regarding basic research on the relationship between human corneal endothelial cells and endoplasmic reticulum stress. Non Patent Literature 3 is a document regarding basic research on the relationship between human corneal endothelial cells and oxidative stress.

CITATION LIST

Non Patent Literature

[NPL 1] Onouchi H. et al., Biomedical Gerontology: Vol. 34, No. 2, 51 (2010)
[NPL 2] William L. Corwin et al., Cryobiology: Vol. 63, No. 1, 46-55 (2011)
[NPL 3] Ula V. Jurkunas et al., Am J Pathol: Vol. 177, No. 5, 2278-2289 (2010)

SUMMARY OF INVENTION

Solution to Problem

Various considerations are required in order to maintain a corneal endothelium in excellent condition. The inventors have focused on the relationship between the endoplasmic reticulum (ER) stress and corneal endothelial cells among others to discover that the stressed condition can be improved by inhibiting a transforming growth factor-β (TGF-β) pathway and to discover a technique that can treat or prevent ER stress related disorders to complete the present invention. Thus, the present invention provides the following inventions.

(1) A therapeutic or prophylactic drug for a disease, disorder or condition associated with endoplasmic reticulum (ER) stress in a corneal endothelium, comprising a TGFβ signal inhibitor.
(2) The therapeutic or prophylactic drug of item (1), wherein the disease, disorder or condition is a disorder related to Fuchs' endothelial corneal dystrophy.
(3) The therapeutic or prophylactic drug of item (1) or (2), wherein the therapeutic or prophylactic drug suppresses the disease, disorder or condition comprising a disorder of a corneal endothelial cell in Fuchs' endothelial corneal dystrophy.
(4) The therapeutic or prophylactic drug of any one of items (1)-(3), wherein the disease, disorder or condition comprises at least one selected from the group consisting of decreased corneal endothelial density, guttae formation, hypertrophy of the Descemet's membrane, hypertrophy of a cornea, corneal epithelial disorder, turbidity in corneal stroma, photophobia, blurred vision, visual impairment, ophthalmalgia, epiphora, hyperemia, pain, bullous keratopathy, eye discomfort, diminished contrast, glare, and edema of the corneal stroma.
(5) The therapeutic or prophylactic drug of any one of items (1)-(4), wherein the TGFβ signal inhibitor comprises at least one of 4-[4-(1,3-benzodioxole-5-yl)-5-(2-pyridinyl)-1H-imidazole-2-yl]benzamide, BMP-7, an anti-TGF-β antibody, an anti-TGF-β receptor antibody, a siRNA of TGF-β, a siRNA of a TGF-β receptor, a shRNA of TGF-β, a shRNA of a TGF-β receptor, an aptamer of TGF-β, an aptamer of a TGF-β receptor, an antisense oligonucleotide of TGF-β, 6,7-dimethoxy-2-((2E)-3-(1-methyl-2-phenyl-1H-pyrrolo[2,3-b] pyridine-3-yl-prop-2-enoyl))-1,2,3,4-tetrahyrdoisoquinolone, 3-(6-methyl-2-pyridinyl)-N-phenyl-4-(4-quinolinyl)-1H-pyrazole-1-carbothioamide, 2-(3-(6-methylpyridine-2-yl)-1H-pyrazole-4-yl)-1,5-naphthyridine, 6-(4-(piperidine-1-yl) ethoxy)phenyl)-3-(pyridine-4-yl) pyrazolo[1,5-a]pyrimidine, 2-(5-chloro-2-fluorophenyl)-4-[(4-pyridinyl)amino]pteridine, 4-[3-(2-pyridinyl)-1H-pyrazole-4-yl]-quinoline, A-83-01 (3-(6-methyl-2-pyridinyl)-N-phenyl-4-(4-quinolinyl)-1H-pyrazole-1-carbothioamide), a pharmaceutical acceptable salt or solvate thereof, or a solvate of a pharmaceutically acceptable salt thereof.
(6) The therapeutic or prophylactic drug of any one of items (1)-(5), wherein the TGF-β signal inhibitor comprises 4-[4-(1,3-benzodioxole-5-yl)-5-(2-pyridinyl)-1H-imidazole-2-yl]benzamide or a pharmaceutically acceptable salt thereof.
(7) The therapeutic or prophylactic drug of any one of items (1)-(6), wherein the corneal endothelium is from a primate.
(8) The therapeutic or prophylactic drug of any one of items (1)-(7), wherein the corneal endothelium is from a human.
(9) The therapeutic or prophylactic drug of any one of items (1)-(8), comprising an additional pharmaceutical ingredient.
(10) The therapeutic or prophylactic drug of any one of items (1)-(9), which is eye drops.
(11) A TGFβ signal inhibiting substance for treating or preventing a disorder associated with endoplasmic reticulum (ER) stress in a corneal endothelium.
(11A) The TGFβ signal inhibiting substance of item (11), wherein the TGFβ signal inhibiting substance has a feature of the inhibitor of any one of items (1)-(10).

(12) A method of treating or preventing a disorder associated with endoplasmic reticulum (ER) stress in a corneal endothelium in a subject, wherein the method comprises a step of administering an effective amount of a TGFβ signal inhibitor to the subject.

(12A) The method of item (12) having the feature of any one of items (1)-(10).

In another aspect, the present invention provides the following inventions.

(A1) A therapeutic or prophylactic drug for a disease, disorder or condition associated with endoplasmic reticulum (ER) stress in a corneal endothelium, comprising a TGF-β signal inhibitor.

(A2) The therapeutic or prophylactic drug of item (A1), wherein the disease, disorder or condition is associated with mitochondrial failure.

(A3) The therapeutic or prophylactic drug of item (A1) or (A2), wherein the disease, disorder or condition is associated with apoptosis due to mitochondrial failure.

(A4) The therapeutic or prophylactic drug of any one of items (A1)-(A3), wherein the disease, disorder or condition is related to Fuchs' endothelial corneal dystrophy.

(A5) The therapeutic or prophylactic drug of any one of items (A1)-(A4), wherein the therapeutic or prophylactic drug suppresses the disease, disorder or condition comprising a disorder of a corneal endothelial cell in Fuchs' endothelial corneal dystrophy.

(A6) The therapeutic or prophylactic drug of any one of items (A1)-(A5), wherein the therapeutic or prophylactic drug suppresses at least one of the disease, disorder or condition selected from the group consisting of decreased corneal endothelial density, guttae formation, hypertrophy of the Descemet's membrane, hypertrophy of a cornea, corneal epithelial disorder, turbidity in corneal stroma, photophobia, blurred vision, visual impairment, ophthalmalgia, epiphora, hyperemia, pain, bullous keratopathy, eye discomfort, diminished contrast, glare, and edema of the corneal stroma.

(A7) The therapeutic or prophylactic drug of any one of items (A1)-(A6), wherein the TGF-β signal inhibitor comprises at least one of 4-[4-(1,3-benzodioxole-5-yl)-5-(2-pyridinyl)-1H-imidazole-2-yl]benzamide, BMP-7, an anti-TGF-β antibody, an anti-TGF-β receptor antibody, a siRNA of TGF-β, a siRNA of a TGF-β receptor, a shRNA of TGF-β, a shRNA of a TGF-β receptor, an aptamer of TGF-β, an aptamer of a TGF-β receptor, an antisense oligonucleotide of TGF-β, 6,7-dimethoxy-2-((2E)-3-(1-methyl-2-phenyl-1H-pyrrolo[2,3-b]pyridine-3-yl-prop-2-enoyl))-1,2,3,4-tetrahydroisoquinolone, 3-(6-methyl-2-pyridinyl)-N-phenyl-4-(4-quinolinyl)-1H-pyrazole-1-carbothioamide, 2-(3-(6-methylpyridine-2-yl)-1H-pyrazole-4-yl)-1,5-naphthyridine, 6-(4-(piperidine-1-yl)ethoxy)phenyl)-3-(pyridine-4-yl) pyrazolo[1,5-a]pyrimidine, 2-(5-chloro-2-fluorophenyl)-4-[(4-pyridinyl)amino]pteridine, 4-[3-(2-pyridinyl)-1H-pyrazole-4-yl]-quinoline, A-83-01 (3-(6-methyl-2-pyridinyl)-N-phenyl-4-(4-quinolinyl)-1H-pyrazole-1-carbothioamide), a pharmaceutical acceptable salt or solvate thereof, or a solvate of a pharmaceutically acceptable salt thereof.

(A8) The therapeutic or prophylactic drug of any one of items (A1)-(A7), wherein the TGF-β signal inhibitor comprises 4-[4-(1,3-benzodioxole-5-yl)-5-(2-pyridinyl)-1H-imidazole-2-yl]benzamide or a pharmaceutically acceptable salt thereof.

(A9) The therapeutic or prophylactic drug of any one of items (A1)-(A8), further comprising a therapeutic agent for mitochondrial failure induced by ER stress.

(A10) The therapeutic or prophylactic drug of item (A9), wherein the therapeutic agent for mitochondrial failure induced by ER stress is selected from the group consisting of BiP inducer X (BIX), 4-phenyl butyric acid (PBA), trimethylamine N-oxide (TMAO), tauroursodeoxycholic acid (TUDCA), and teprenone (also sold as selbex).

(A11) The therapeutic or prophylactic drug of any one of items (A1)-(A10), wherein the corneal endothelium is from a primate.

(A12) The therapeutic or prophylactic drug of any one of items (A1)-(A11), wherein the corneal endothelium is from a human.

(A13) The therapeutic or prophylactic drug of any one of items (A1)-(A12), comprising an additional pharmaceutical ingredient.

(A14) The therapeutic or prophylactic drug of any one of items (A1)-(A13), which is eye drops.

(A14A) The therapeutic or prophylactic drug of any one of the above-described items, wherein the disease, disorder or condition is accompanied by increased expression of an aggresome.

(A14B) The therapeutic or prophylactic drug of any one of the above-described items, wherein the disease, disorder or condition is a disease, disorder or condition associated with an aggresome.

(A14C) The therapeutic or prophylactic drug of any one of the above-described items, wherein the disease, disorder or condition is accompanied by abnormal folding of a protein.

(A14D) The therapeutic or prophylactic drug of any one of the above-described items, wherein the disease, disorder or condition is due to abnormal folding of a protein.

(A15) A TGF-β signal inhibiting substance for treating or preventing a disorder associated with endoplasmic reticulum (ER) stress.

(A15A) The TGFβ signal inhibiting substance of item (A15), wherein the TGFβ signal inhibiting substance has a feature of the inhibitor of any one of items (A1)-(A14) and (A14A)-(A14D).

(A16) A method of treating or preventing a disorder associated with endoplasmic reticulum (ER) associated stress in a subject, wherein the method comprises a step of administering an effective amount of a TGF-β signal inhibitor to the subject.

(A16A) The method of item (A16) having the feature of any one of items (A1)-(A14) and (A14A)-(A14D).

Endoplasmic reticulum stress is stress on cells due to accumulation of proteins that were not folded in a normal conformation in the cells. Endoplasmic reticulum stress is not induced in a normal extracellular matrix. In this regard, it was impossible to predict from the knowledge up to this point, such as information related to extracellular matrices, that relief to a cellular disorder due to endoplasmic reticulum stress in Fuchs' endothelial corneal dystrophy of the present invention can be provided by suppressing a TGFβ signal.

The present invention is intended to be able to provide one or more of the aforementioned features in further combinations in addition to the combinations expressly shown. Further embodiments and advantages of the present invention are recognized by those skilled in the art by reading and understanding the following Detailed Description as needed.

Advantageous Effects of Invention

The present invention provides a medicament that can treat or prevent a disease associated with endoplasmic reticulum (ER) stress, which did not have a method of treatment other than corneal transplantation, where the technique can also be materialized as eye drops or the like.

BRIEF DESCRIPTION OF DRAWINGS

The patent or application file contains at least one drawing executed in color. Copies of this patent or patent application publication with color drawing(s) will be provided by the Office upon request and payment of the necessary fee.

FIG. 2 shows morphological abnormality in the endoplasmic reticulum and mitochondria in Fuchs' endothelial corneal dystrophy. The left side shows immobilized human corneal endothelial cells (iHCEC) and the right side shows immobilized cells with Fuchs' endothelial corneal dystrophy (iFECD). Both the top and bottom rows show images from a transmission electron microscope. * indicates a mitochondrion,  indicates endoplasmic reticulum, and * indicates extracellular matrix.

FIG. 14 is a diagram showing that Fuchs' endothelial corneal dystrophy has a high level of denatured proteins and is increased by TGF-β stimulation. The left panel shows pictures of cells of a control (no TGFβ stimulation: top row) and with TGF-β stimulation (10 ng/ml; bottom row) (40-times magnification). Each of the graphs on the top right shows a result from a flow cytometer. From the left, comparison of iHCEC (black) with iFECD (red), comparison of iHCEC (black) with iHCEC+TGFβ (red), and comparison of iFECD (black) with iFECD+TGFβ (red) are shown. The y axis is the cell count and the x axis shows the fluorescence intensity of aggresomes. In the left graph, iHCEC (black) is observed shifted to the left as a whole relative to iFECD (red). In the middle graph, iHCEC (black) is observed to be almost overlapping with iHCEC+TGFβ (red). In the right graph, iFECD (black) is observed shifted to the top left relative to iFECD+TGFβ (red). The bottom right section compares fluorescence intensity of aggresomes for the control with TGFβ stimulated iHCEC and iFECD. The white bar is iHCEC and the black bar is iFECD. * indicates p<0.05.

DESCRIPTION OF EMBODIMENTS

Figure 1:
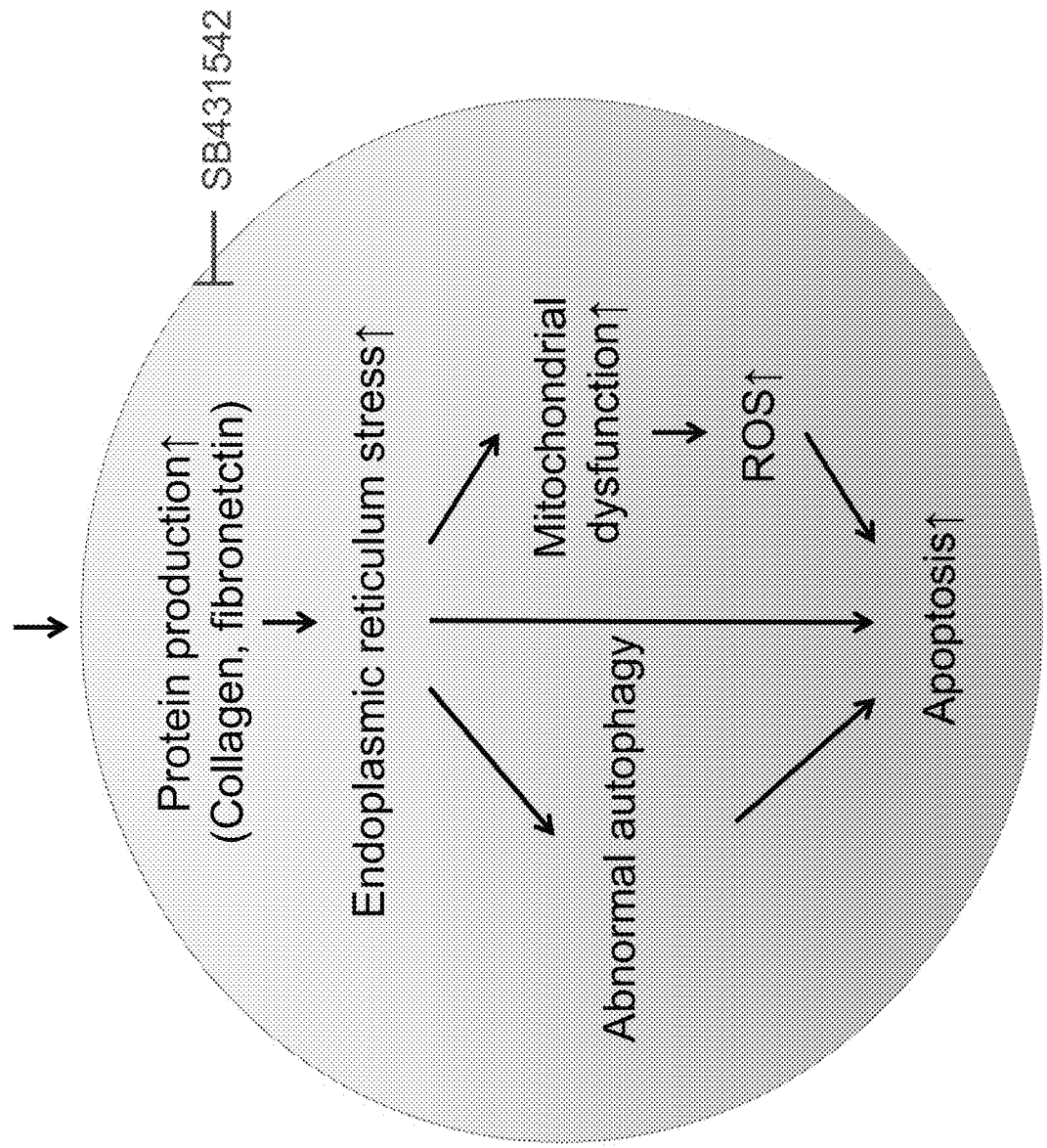
FIG. 1 shows a hypothetical scheme of pathology of a disease associated with endoplasmic reticulum stress (e.g., Fuchs' endothelial corneal dystrophy) focused on the relationship between endoplasmic reticulum stress and apoptosis based on the present invention.

The present invention is described hereinafter. Throughout the entire specification, a singular expression should be understood as encompassing the concept thereof in the plural form unless specifically noted otherwise. Thus, singular articles (e.g., "a", "an", "the" and the like in case of English) should also be understood as encompassing the concept thereof in the plural form unless specifically noted otherwise. Further, the terms used herein should be understood as being used in the meaning that is commonly used in the art, unless specifically noted otherwise. Thus, unless defined otherwise, all terminologies and scientific technical terms that are used herein have the same meaning as the terms commonly understood by those skilled in the art to which the present invention pertains. In case of a contradiction, the present specification (including the definitions) takes precedence.

Definition

As used herein, "iFECD" (immobilized Fuchs' endothelial corneal dystrophy) is an abbreviation for immobilized cells with Fuchs' endothelial corneal dystrophy.

As used herein, "HCEC" is an abbreviation for human corneal endothelial cells. In addition, "iHCEC" is an abbreviation for immobilized human corneal endothelial cells.

As used herein, "transforming growth factor-β (also denoted with the abbreviation TGF-β)" is used in the same meaning as those used in the art. It is a homodimer multifunctional cytokine with a molecular weight of 25 kD exhibiting a variety of biological activity, such as being responsible for pathogenesis of various sclerotic diseases, rheumatoid arthritis, and proliferative vitreoretinopathy, being deeply involved in hair loss, suppressing the functioning of immunocompetent cells while suppressing overproduction of protease to prevent degradation of pulmonary tissue resulting in pulmonary emphysema, and suppressing cancer cell growth. In humans, there are three isoforms, TGF-β1 to β3. TGF-β is produced as an inactive latent form with a molecular weight of about 300 kD which is unable to bind to a receptor. The action thereof is exerted by being activated on a target surface or the surroundings thereof to become an active form that can bind to a receptor.

Although not wishing to be bound by any theory, the action of TGF-β in a target cell is understood, to be transmitted by a phosphorylation channel of a series of proteins responsible for transmitting information called Smad. First, when activated TGF-β binds to a TGF-β type II receptor on a target cell surface, a receptor complex is formed, consisting of two molecules of type II receptors and two molecules of TGF-β type I receptors, and the type II receptors phosphorylate the type I receptors. It is understood that when the phosphorylated type I receptors then phosphorylate Smad2 or Smad3, Smad2 or Smad3 form a complex with Smad4, which migrates to a nucleus and binds to a target sequence called CAGA box present in a target gene promotor region to induce transcription and expression of a target gene with a coactivator.

A transforming growth factor-β (TGF-β) signaling pathway can modulate many cellular activities, such as cell growth and differentiation, growth arrest, apoptosis, and epithelial mesenchymal transition (EMT), by modulating the target gene. Members of the TGF-β family including TGF-β itself (e.g., TGF-β1, TGF-β2, and TGF-β3), activin, and bone morphogenetic proteins (BMP) are potent modulators of cell growth, differentiation, migration and apoptosis.

TGF-β is a protein of about 24 kb produced by many cells including B cells, T cells, and activated macrophages and by many other cell types. Effects of TGF-β on the immune system include IL-2 receptor induction, inhibition of IL-1 induced thymocyte growth, and blocking of IFN-γ induced macrophage activation. TGF-β is considered to be involved in various pathological conditions (Border et al. (1992) J. Clin. Invest. 90:1) and is thoroughly proven to function as either a tumor suppressing substance or a tumor promotor.

Signaling of TGF-β is mediated by two serine/threonine kinase cell surface receptors TGF-βRII and ALK5. TGF-β signaling is initiated by ligand induced receptor dimerization enabling TGF-βRII to phosphorylate an ALK5 receptor. The phosphorylation activates ALK5 kinase activity, and the activated ALK5 then phosphorylates a downstream effector Smad protein (vertebrate homologue of MAD or "Mothers against DPP (decapentaplegic)" protein, Smad2 or Smad 3. A p-Smad2/3 complex with Smad4 enters a nucleus and activates transcription of a target gene.

Smad3 is a member of the R-Smad (receptor-activated Smad) subgroup of Smad and a direct mediator of transcription activation by a TGF-β receptor. A TGF-β stimulation results in phosphorylation and activation of Smad2 and Smad3, which form a complex with Smad4 ("common Smad" or "co-Smad" in vertebrates). This accumulates with the nucleus and modulates transcription of a target gene. R-Smad is localized in a cytoplasm and forms a complex with co-Smad in ligand induced phosphorylation by a TGF-β receptor, migrates to the nucleus, where it modulates gene expression associated with a cooperative transcription factor and chromatin. Smad6 and Smad7 are each inhibitory Smad ("I-Smad"), that is, they are transcriptionally induced by TGF-β and function as a TGF-β signaling inhibitor (Feng et al. (2005) Annu. Rev. Cell. Dev. Biol. 21:659). Smad6/7 obstruct receptor-mediated activation of R-Smad to exert their inhibitory effect; and they are associated with a type I receptor, which competitively obstructs mobilization and phosphorylation of R-Smad. Smad6 and Smad7 are known to replenish E3 ubiquitin ligase, which induces ubiquitination and degradation of Smad6/7 interacting proteins.

In one embodiment, the disease, disorder or condition targeted by the present invention is accompanied by increased expression of an aggresome. Alternatively, the disease, disorder or condition targeted by the present invention is a disease, disorder or condition associated with an aggresome.

In another embodiment, the disease, disorder or condition targeted by the present invention is accompanied by abnormal folding of a protein. Alternatively, the disease, disorder or condition targeted by the present invention is due to abnormal folding of a protein.

In mammalian cells, it is known that proteins aggregated due to being unfolded, misfolding, abnormality in protein degradation or the like (also referred to as incompletely folded protein or denatured protein (unfolded protein)) are ubiquitinated and accumulated near the centrosome by a dynein motor moving in microtubules to form an inclusion body called an aggresome. In general, aggresomes are formed by a thermal shock, viral infection, oxidative stress or the like. Some diseases are known in humans involving inclusion bodies in a cell, such as Lewy bodies seen in nerve cells in Parkinson's disease, Mallory bodies seen in liver cells in alcoholic liver diseases, and glass-like bodies seen in astrocytes in amyotrophic lateral sclerosis.

TGF-β signaling pathways further have other pathways using BMP-7 transmission or the like, which go through ALK-1/2/3/6 via Smad1/5/8 to express a function. For TGF-β signaling pathways, see J. Massagu'e, Annu. Rev. Biochem. 1998. 67: 753-91; Vilar J M G, Jansen R, Sander C (2006) PLoS Comput Biol 2 (1):e3; Leask, A., Abraham, D. J. FASEB J. 18, 816-827 (2004); Coert Margadant & Arnoud Sonnenberg EMBO reports (2010) 11, 97-105; Joel Rosenbloom et al., Ann Intern Med. 2010; 152: 159-166 and the like.

As used herein, "transforming growth factor (TGF)-β signal inhibitor" refers to any factor that inhibits TGF signaling. TGF-β, when antagonizing, may be referred to as an antagonist. However, as is used in the present invention, TGF-β antagonists are encompassed by TGF-β signal inhibitors. Since such an inhibitor is generally a substance, a "TGF-β signal inhibiting substance" can be used interchangeably with "TGF-β signal inhibitor". "TGF-β" may also be denoted herein as "TGFβ" in the same meaning.

Thus, typical TGF-β signal inhibitors used in the present invention include, but are not limited to, TGF-β antagonists, TGF-β receptor antagonists, Smad3 inhibitors, ligand traps (decoy receptors, antibodies to a ligand), antisense oligonucleotides, TGF-β receptor kinase inhibitors, peptide aptamers, siRNAs, shRNAs and the like (see Connolly E., et al. Int. J. Biol. Sci. 2012; 8(7): 964-978 FIG. 3 and the like).

Examples of TGF-β signal inhibitors that can be used in the present invention include, but are not limited to, SB431542 (4-[4-(1,3-benzodioxole-5-yl)-5-(2-pyridinyl)]-1H-imidazole-2-yl]benzamide), BMP-7, anti-TGF-β antibodies, anti-TGF-β receptor antibodies, siRNAs of TGF-β, siRNAs of a TGF-β receptor, antisense oligonucleotides of TGF-β, 6,7-dimethoxy-2-((2E)-3-(1-methyl-2-phenyl-1H-pyrrolo[2,3-b] pyridine-3-yl-prop-2-enoyl))-1,2,3,4-tetrahydroisoquinolone, A83-01 (3-(6-methyl-2-pyridinyl)-N-phenyl-4-(4-quinolinyl)-1H-pyrazole-1-carbothioamide), Stemolecule™ TLK inhibitors (2-(3-(6-methylpyridine-2-yl)-1H-pyrazole-4-yl)-1,5-naphthyridine), Stemolecule™ BMP inhibitor LDN-193189 (6-(4-(piperidine-1-yl)ethoxy) phenyl)-3-(pyridine-4-yl) pyrazolo[1,5-a]pyrimidine), SD-208 (2-(5-chloro-2-fluorophenyl)-4-[(4-pyridinyl) amino]pteridine), LY364947 (4-[3-(2-pyridinyl)-1H-pyrazole-4-yl]-quinoline), a pharmaceutically acceptable salt or a solvate thereof, a solvate of a pharmaceutically acceptable salt thereof, and the like. The TGF-β signal inhibitors, compositions, medicaments, therapeutic drugs, and prophylactic drugs of the present invention can have a neutral form, salt form or mixed with another prodrug (e.g., ester or the like). As used herein, "salt" includes, for example, anionic salts formed with any acidic (e.g., carboxyl) group and cationic salts formed with any basic (e.g., amino) group. Salts include inorganic and organic salts, including for example salts described in Berge et al., J. Pharm. Sci., 1977, 66, 1-19. Further, salts include, for example, metal salts, ammonium salts, salts with organic base, salts with inorganic acid, salts with organic acid and the like. In one embodiment of the present invention, "solvate" is a compound formed with a solute and a solvent. For instance, J. Honig et al., The Van Nostrand Chemist's Dictionary P650 (1953) can be referred to for solvates. When the solvent is water, the resulting solvate is a hydrate. Such a solvent preferably does not obstruct biological activity of a solute. Examples of such a preferred solvent are not particularly limited, but include water and various buffers. In one embodiment of the present invention, examples of "chemical modification" include modification by PEG or a derivative thereof, fluorescein modification, biotin modification and the like. Pharmaceutically acceptable salts include those formed with a free carboxyl group from hydrochloric acid, phosphoric acid, acetic acid, oxalic acid, tartaric acid or the like, those formed with a free amine group such as those from isopropylamine, triethylamine, 2-ethylaminoethanol, histidine, procaine or the like, and those derived from sodium, potassium, ammonium, calcium, ferric hydroxide or the like.

Other TGF-β signal inhibitors include, but are not limited to, monoclonal and polyclonal antibodies to one or more isoforms of TGF-β (U.S. Pat. No. 5,571,714; also see International Publication No. WO 97/13844 and International Publication No. WO 00/66631), TGF-β receptors, soluble forms of such a receptor (e.g., soluble TGF-β type III receptor), or antibodies directed to a TGF-β receptor (U.S. Pat. Nos. 5,693,607, 6,001,969, 6,010,872, 6,086,867, 6,201,108; International Publication No. WO 98/48024; International Publication No. WO 95/10610; International Publication No. WO 93/09228; International Publication No. WO 92/00330), latency associated peptides (International Publication No. WO 91/08291), large latent TGF-β (International Publication No. WO 94/09812), fetuin (U.S.

Pat. No. 5,821,227), decorin and other proteoglycans such as biglycan, fibromodulin, lumican, and endoglin (International Publication No. WO 91/10727; U.S. Pat. Nos. 5,654,270, 5,705,609, 5,726,149; 5,824,655; International Publication No. WO 91/04748; U.S. Pat. Nos. 5,830,847, 6,015,693; International Publication No. WO 91/10727; International Publication No. WO 93/09800; and International Publication No. WO 94/10187), somatostatin (International Publication No. WO 98/08529), mannose-6-phosphoric acid or mannose-1-phosphoric acid (U.S. Pat. No. 5,520,926), prolactin (International Publication No. WO 97/40848), insulin-like growth factor II (International Publication No. WO 98/17304), IP-10 (International Publication No. WO 97/00691), Arg-Gly-Asp-containing peptides (Pfeffer, U.S. Pat. No. 5,958,411; International Publication No. WO 93/10808), plant, fungus and bacterial extracts, (EP-A-813875; Japanese Laid-Open Publication No. 8-119984; and Matsunaga et al., U.S. Pat. No. 5,693,610), antisense oligonucleotides (U.S. Pat. Nos. 5,683,988; 5,772,995; 5,821,234, 5,869,462; and International Publication No. WO 94/25588), proteins associated with TGF-β signaling including Smad and MAD (EP-A-874046; International Publication No. WO 97/31020; International Publication No. WO 97/38729; International Publication No. WO 98/03663; International Publication No. WO 98/07735; International Publication No. WO 98/07849; International Publication No. WO 98/45467; International Publication No. WO 98/53068; International Publication No. WO 98/55512; International Publication No. WO 98/56913; International Publication No. WO 98/53830; International Publication No. WO 99/50296; U.S. Pat. Nos. 5,834,248; 5,807,708; and 5,948,639), Ski and Sno (Vogel, 1999, Science, 286:665; and Stroschein et al., 1999, Science, 286:771 to 774), one or more single-stranded oligonucleotide aptamers or an expression plasmid encoding them, suitable for inhibiting or interfering with the binding of TGF-β to a receptor of the same origin, and any mutant, fragment or derivative of a molecule identified above, which retains an ability to inhibit the activity of TGF-β. The TGF-β inhibitor may be a TGF-β antagonist, and may be a human monoclonal antibody or a humanized monoclonal antibody (or F(ab)$_2$ fragment, Fv fragment, single chain antibody, and other forms or fragments of an antibody retaining the ability to bind to TGF-β, a fragment thereof or the like), which blocks TGF-β binding to a receptor. The TGF-β receptor and a TGF-β binding fragment, and especially a soluble fragment, of the TGF-β receptor are TGF-β antagonists which are useful in the method according to the present invention. In a certain embodiment, an inhibitor with a preferred TGF-β function is a soluble TGF-β receptor, and especially a TGF-β type II receptor (TGFBIIR) or a TGF-β type III receptor (TGFBIIIR or beta glycan) including, for example, extracellular domain of TGFBIIIR or TGFBIIR, preferably a recombinant soluble TGF-β receptor (rsTGFBIIR or rsTGFBIIIR). The TGF-β receptor and a TGF-β binding fragment of the TGF-β receptor, especially a soluble fragment, are TGF-β antagonists useful in the method according to the present invention. TGF-β receptors and nucleic acids encoding them are well known in the art. A nucleic acid sequence encoding type 1 TGF-β receptor is disclosed in GenBank accession number L15436 and U.S. Pat. No. 5,538,892 (Donahoe et al.). A nucleic acid sequence of a TGF-β type 2 receptor is publicly available under GenBank accession numbers AW236001, AI35790, AI279872, AI074706, and AA808255. A nucleic acid sequence of a TGF-β type 3 receptor is also publicly available under GenBank accession numbers NM003243, AI887852, AI817295, and AI681599.

In addition, still other TGF-β signal inhibitors or antagonists and manufacturing methods thereof are well known in the art in addition to many that are currently under development. Since any effective TGF-β antagonist may be useful in the method according to the present invention, specific TGF-β signal inhibitors or antagonists used are not those with limited characteristics. Examples of such antagonists include monoclonal and polyclonal antibodies to TGF-β of one or more isotypes (U.S. Pat. No. 5,571,714 and International Publication No. WO 97/13844), TGF-β receptors, a fragment thereof, a derivative thereof, and antibodies to a TGF-β receptor (U.S. Pat. Nos. 5,693,607, 6,008,011, 6,001,969 and 6,010,872, and International Publication No. WO 92/00330, International Publication No. WO 93/09228, International Publication No. WO 95/10610, and International Publication No. WO 98/48024); latency-associated peptides (International Publication No. WO 91/08291), large latent TGF-β (International Publication No. WO 94/09812), fetuin (U.S. Pat. No. 5,821,227), decorin and other proteoglycans such biglycan, fibromodulin, lumican, endoglin (U.S. Pat. Nos. 5,583,103, 5,654,270, 5,705,609, 5,726,149, 5,824,655, 5,830,847, 6,015,693, and International Publication No. WO 91/04748, International Publication No. WO 91/10727, International Publication No. WO 93/09800 and International Publication No. WO 94/10187).

Further examples of such an antagonist include hosts of other proteins associated with TGF-β signaling, including somatostatin (International Publication No. WO 98/08529), mannose-6-phosphoric acid or mannose-1-phosphoric acid (U.S. Pat. No. 5,520,926), prolactin (International Publication No. WO 97/40848), insulin-like growth factor II (International Publication No. WO 98/17304), IP-10 (International Publication No. WO 97/00691), arginine (arg)-glycine (gly)-asparagine acid (asp)-containing peptides (U.S. Pat. No. 5,958,411 and International Publication No. WO 93/10808), plans, fungus and bacteria extracts (European Patent Application Publication No. 813875, Japanese Laid-Open Publication No. 8-119984 and U.S. Pat. No. 5,693,610), antisense oligonucleotides (U.S. Pat. Nos. 5,683,988, 5,772,995, 5,821,234 and 5,869,462, and International Publication No. WO 94/25588), and Smad and MAD (European Patent Application No. EP 874046, International Publication No. WO 97/31020, International Publication No. WO 97/38729, International Publication No. WO 98/03663, International Publication No. WO 98/07735, International Publication No. WO 98/07849, International Publication No. WO 98/45467, International Publication No. WO 98/53068, International Publication No. WO 98/55512, International Publication No. WO 98/56913, International Publication No. WO 98/53830 and International Publication No. WO 99/50296, and U.S. Pat. Nos. 5,834,248, 5,807,708 and 5,948,639), and Ski and Sno (G. Vogel, Science, 286:665 (1999) and Stroschein et al., Science, 286:771-74 (1999)), and any fragment and derivative of the above-mentioned molecules retaining the ability to inhibit the activity of TGF-β.

The TGF-β antagonists suitable for the use in the present invention also include functional mutants, mutants, derivatives, and analogues of the aforementioned TGF-β antagonists so long as their ability of inhibiting the amount or activity of TGF-β is retained. The "mutant", "derivative", and "analogue" as used herein refer to a molecule having a form or structure similar to that of its parent compound and retaining the ability to act as a TGF-β antagonist. For example, any of the TGF-β antagonists disclosed herein may be crystallized, and useful analogues may be rationally designed based on coordinates responsible for shaping (one or more) active sites. Instead; those skilled in the art can alter a functional group of a known antagonist or screen for such an altered molecule with respect to increase in activity, half-life, bioavailability, or other desirable characteristics, without unnecessary experiments. When the TGF-β antagonist is a polypeptide, a fragment and variant of the polypeptide may be produced to increase the ease of delivery, activity, half-life or the like (e.g., humanized antibodies or functional antibody fragments discussed above). Considering the technical level in the art for producing synthetic and recombinant polypeptides, such a variant may be attained without unnecessary experiments. Those skilled in the art may also design a novel inhibitor based on knowledge on a crystal structure and/or active site of the TGF-β inhibitor as described herein. A polypeptide inhibitor, such as a soluble TGF-β receptor, may be effectively introduced through gene transfer. Thus, a certain embodiment for the method according to the present invention includes use of a vector suitable for expression of a TGF-β receptor or a binding partner, preferably a soluble receptor or a soluble binding partner. In a preferred embodiment, administration of a soluble TGF-β antagonist can be achieved by gene transfer which uses a vector comprising a cDNA encoding a soluble antagonist or cDNA encoding an extracellular domain of a TGF-β type II receptor (rsTGFBIIR) or a TGF-β type III receptor (rsTGFBIIIR). As this vector, any suitable vector can be used, which causes in situ expression of a soluble TGF-β antagonist in a cell transfected using the vector, inhibits the activity of TGF-β, and suppresses TGF-β-mediated fibrogenesis. Preferred vectors include an adenovirus vector, a lentivirus vector, an Epstein-Barr virus (EBV) vector, an adeno-associated virus (AAV) vector, and a retrovirus vector, developed for the purpose of gene transfer. Other non-vector methods for gene transfer may also be used, such as lipid/DNA complex, protein/DNA conjugate and naked DNA transfer methods. Further suitable TGF-β antagonists developed for delivery via adenovirus gene transfer include, but are not limited to, a chimeric cDNA encoding an extracellular domain of a TGF-β type II receptor, fused to an Ig Fc domain (Isaka et al., 1999, Kidney Int., 55: pp. 465 to 475), an adenovirus gene transfer vector of a dominant negative mutant of a TGF-β type II receptor (Zhao et al., 1998, Mech. Dev., 72: pp. 89 to 100), and an adenovirus gene transfer vector of decorin, which is a TGF-β binding proteoglycan (Zhao et al., 1999, Am. J. Physiol., 277: pp. L412 to L422). Adenovirus-mediated gene transfer has extremely high efficiency relative to other gene delivery forms.

TGF-β receptors, TGF-β binding fragments and soluble fragments of the TGF-β receptor and the like are TGF-β antagonists useful in the present invention. TGF-β receptors and nucleic acids encoding them are well known in the art. Nucleic acid sequences encoding a TGF-β type 1 receptor are disclosed in GenBank accession number L15436 and U.S. Pat. No. 5,538,892 by Donahoe et al. Nucleic acid sequences of a TGF-β type 2 receptor are also publicly available under GenBank accession numbers AW236001; AI35790; AI279872; AI074706; and AA808255. Nucleic acid sequences of a TGF-β type 3 receptor are also publicly available under GenBank accession numbers NM003243; AI887852; AI817295; and AI681599. In one exemplary embodiment, a TGF-β antagonist is an antibody which blocks TGF-β binding to a receptor thereof, or to a F(ab)$_2$ fragment, a Fv fragment, a single-stranded antibody, and a fragment of other "antibody" forms retaining the ability to bind to TGF-β. Such an antibody may be chimerized or humanized. Herein, a chimerized antibody includes a constant region of a human antibody and a variable region of a non-human antibody such as a murine antibody. A humanized antibody includes a constant region and a framework variable region (i.e., variable regions other than hypervariable regions) of a human antibody, and a hypervariable region of a non-human antibody such as a murine antibody. As a matter of course, such an antibody may be any other type of antibody derivative, such as a human antibody selected or picked from a phage display system or produced from a XenoMouse.

Findings related to Smad are increasing. A TGF-β signaling pathway is initiated when a molecule thereof binds to a heterodimer cell surface complex consisting of type I (TbRI) and type II (TbRII) serine/threonine kinase receptors to provoke this heterodimer cell surface complex. Then, the heterodimer receptor transmits the signal through phosphorylation of a target Smad protein downstream. As described above, there are three functional classes for Smad proteins, which are Smad (R-Smad) regulated by a receptor such as Smad2 and Smad3, a co-mediator (Co-Smad) which is also referred to as Smad4, and an inhibitor Smad (I-Smad). After phosphorylation by the heterodimer receptor complex, R-Smad forms a complex with Co-Smad, moves to the nucleus, and modulates transcription of the target gene in cooperation with each of the other proteins (Derynck, R., et al. (1998) Cell 95: 737-740); Massague, J. and Wotton, D. (2000) EMBO J. 19:1745). A nucleotide sequence and an amino acid sequence of human Smad3 are disclosed in, for example, GenBank Accession No. gi: 42476202. A nucleotide sequence and an amino acid sequence of murine Smad3 are disclosed in, for example, GenBank Accession No. gi: 31543221. As described above, a TGF-β stimulation results in phosphorylation and activation of Smad2 and Smad3, which form a complex with Smad4 (also referred to as "common Smad" or "co-Smad"), and the complex accumulates with a nucleus to modulate the transcription of the target gene. Thus, TGF-β signal inhibition may also be achieved by inhibition of Smad2, 3 or co-Smad (Smad4). R-Smad is localized in a cytoplasm and forms a complex with co-Smad through ligand-induced phosphorylation by a TGF-β receptor and move to a nucleus, where they modulate gene expression associated with chromatin and a cooperative transcription factor. Thus, TGF-β signal inhibition can also be achieved by directly or indirectly inhibiting R-Smad. Smad6 and Smad7 are inhibitor Smad (I-Smad), that is, they are transcriptionally induced by TGF-β to function as an inhibitor of TGF-β signaling (Feng et al., (2005) Annu. Rev. Cell. Dev. Biol. 21: 659). Smad6/7 obstructs receptor-mediated activation of R-Smad to exert an inhibitory effect thereof. They are associated with a type I receptor, which competitively obstructs mobilization and phosphorylation of R-Smad. Smad6 and Smad7 are known to replenish E3 ubiquitin ligase, which induces ubiquitination and degradation of Smad6/7 interacting proteins. Thus, Smad6 and 7 can function as a TGF-β signal inhibitor in the present invention.

Inhibitors of Smad3 that may be used in the present invention include, but are not limited to, antisense nucleotides, siRNAs, antibodies and the like, in addition to, as a low-molecular compound, 6,7-dimethoxy-2-((2E)-3-(1-methyl-2-phenyl-1H-pyrrolo[2,3-b]pyridine-3-yl-prop-2-enoyl))-1,2,3,4-tetrahydroisoquinolone, and the like available from Calbiochem.

As used herein, "substance (e.g., nucleic acid) for suppressing expression (of TGF-β or the like)" is not particularly limited as long as it is a substance which suppresses transcription of an mRNA of a target gene, a substance (e.g., nucleic acid) which degrades a transcribed mRNA, or a substance (e.g., nucleic acid) which suppresses translation of a protein from an mRNA. Examples of such substances include siRNAs, antisense oligonucleotides, ribozyme, expression vectors thereof and other nucleic acids, among which a siRNA and expression vector thereof are preferred, and a siRNA is particularly preferred. "Substance which suppresses expression of a gene" includes proteins, peptides, and other small molecules in addition to those described above. It should be noted that a target gene in the present invention refers to any gene that is associated with a TGF-β signaling pathway.

A method utilizing an antisense technique is well known to those skilled in the art as a method for inhibiting the expression of a specific endogenous gene such as TGF-β, which is targeted in the present invention. As actions of an antisense nucleic acid to inhibit the expression of a target gene, there are a plurality of factors, i.e., inhibition of transcript initiation due to triplex formation; inhibition of transcription due to hybrid formation with a site where an open loop structure is locally formed by RNA polymerase; inhibition of transcription due to hybrid formation with an RNA whose synthesis is about to progress; splicing inhibition due to hybrid formation at a junction of intron and exon; splicing inhibition due to hybrid formation with spliceosome formation site inhibition of migration from a nucleus to cytoplasm due to hybrid formation with an mRNA; splicing inhibition due to hybrid formation with a capping site or a poly (A) addition site; inhibition of translation initiation due to hybrid formation with a translation initiation factor binding site; translational inhibition due to hybrid formation with a ribosome binding site near an initiation codon; inhibition of elongation of a peptide chain due to hybrid formation with a polysome binding site or a translation region of an mRNA; gene expression inhibition due to hybrid formation with an interaction site of a nucleic acid and a protein, and the like. In this manner, an antisense nucleic acid inhibits various processes, such as transcription, splicing and translation, to inhibit the expression of a target gene (Hirashima and Inoue, Shinsei Kagaku Jikken Kouza [*New Biochemical Experiment Course*] 2, Nucleic Acid, IV Idenshi no Fukusei to Hatsugen [*Duplication and Expression of Gene*], Edited by the Japanese Biochemical Society, Tokyo Kagaku Dojin, 1993, 319-347).

The antisense nucleic acid used in the present invention may inhibit the expression and/or function of a gene (nucleic acid) encoding a member of a signaling pathway of the TGF-β described above or the like by any of the above-described actions. In one embodiment, it is considered effective for inhibiting translation of a gene to design an antisense sequence complementary to a non-translation region near the 5' terminal of an mRNA of a gene encoding the TGF-β described above or the like. Further, it is possible to use a sequence complementary to a coding region or a 3' non-translation region. In this manner, nucleic acids comprising an antisense sequence of a sequence of not only a translation region, but also a non-translation region of a gene encoding TGF-β described above or the like are encompassed by the antisense nucleic acids that are used in the present invention. An antisense nucleic acid used is linked downstream of an appropriate promoter, and is preferably linked to a sequence including a transcription termination signal on the 3' end. A nucleic acid prepared in such a manner can be transformed into a desired animal (cell) using a known method. While the sequence of an antisense nucleic acid is preferably a sequence complementary to a gene encoding TGF-β or the like of an animal (cell) to be transformed or a part thereof, it is not necessarily fully complementary as long as the sequence can effectively suppress the expression of genes. The transcribed RNA is preferably 90% or more, and most preferably 95% or more complementary to a transcription product of a target gene. In order to effectively inhibit the expression of a target gene using an antisense nucleic acid, the antisense nucleic acid is preferably at least 12 bases or more but less than 25 bases long. However, the antisense nucleic acid according to the present invention is not necessarily limited to this length. The length may be, for example, 11 bases or less, 100 bases or more, or 500 bases or more. While an antisense nucleic acid may be composed of only DNAs, it may also include nucleic acids other than DNAs, such as locked nucleic acid (LNA). In one embodiment, the antisense nucleic acid used in the present invention may be an LNA-containing antisense nucleic acid including LNA at the 5' terminal or the 3' terminal. In an embodiment where an antisense nucleic acid is used in the present invention, an antisense sequence can be designed based on a nucleic acid sequence of TGF-β or the like using a method described in, for example, Hirashima and Inoue, Shinsei Kagaku Jikken Kouza [*New Biochemical Experiment Course*] 2, Nucleic Acid, IV Idenshino Fukuseito Hatsugen [*Duplication and Expression of Gene*], Edited by the Japanese Biochemical Society, Tokyo Kagaku Dojin, 1993, 319-347, for example.

The expression of TGF-β or the like can also be inhibited by using ribozyme or DNA encoding ribozyme. A ribozyme refers to an RNA molecule having catalytic activity. There are ribozymes with various types of activities, but researches focusing on a ribozyme as an enzyme for cleaving an RNA have made it possible to design a ribozyme for cleaving the RNA in a site-specific manner. While there are ribozymes with 400 nucleotides or more in size, such as group I intron ribozymes and Ml RNA included in RNase P, there are also ribozymes having an activity domain of about 40 nucleotides, such as those referred to as hammer head and hairpin ribosomes (Makoto Koizumi and Elko Ohtsuka, Protein Nucleic Acid And Enzyme, 1990, 35, 2191).

For example, the self-cleaving domain of a hammer head ribozyme cleaves the 3' side of C15 in a sequence called G13U14C15. The base-pair formation of U14 and A9 is considered important for the activity thereof. In addition, it is demonstrated that cleavage can be made at A15 or U15 instead of C15 (Koizumi, M. et al., FEBS Lett, 1988, 228, 228). A ribozyme with a substrate binding site complementary to an RNA sequence near a target site can be designed to create a restriction enzyme-like RNA cleaving ribozyme which recognizes a sequence such as UC, UU or UA in a target RNA (Koizumi, M. et al., FEBS Lett, 1988, 239, 285, Makoto Koizumi and Eiko Ohtsuka, Protein Nucleic Acid And Enzyme, 1990, 35, 2191, Koizumi, M. et al., Nucl. Acids Res., 1989, 17, 7059).

Further, hairpin ribozymes are also useful for the purpose of the present invention. Such a ribozyme is found in, for example, a negative strand of a satellite RNA of tobacco ringspot virus (Buzayan, J M., Nature, 1986, 323, 349). It is also demonstrated that a target-specific RNA cleaving ribozyme can be created from hairpin ribozymes (Kikuchi, Y. & Sasaki, N., Nucl. Acids Res, 1991, 19, 6751, Kikuchi, Yo, Kagaku to Seibutsu [*Chemistry and Organism*], 1992, 30, 112). In this manner, a transcription product of a gene encoding TGF-β or the like can be specifically cleaved using a ribozyme to inhibit the expression of the gene.

Expression of an endogenous gene of TGF-β or the like can also be suppressed by RNA interference (hereinafter, abbreviated as "RNAi") using a double-stranded RNA having a sequence identical or similar to a target gene sequence. RNAi is a technology that is currently drawing attention, where when a double-stranded RNA (dsRNA) is taken up directly into a cell, expression of a gene having a sequence homologous to the dsRNA is suppressed. In mammalian cells, a short strand dsRNA (siRNA) is used so that RNAi can be induced. In comparison to knockout mice, RNAi has many advantages, such as stabile effect, easy experimentation, and low cost. SiRNAs are described in detail in other parts of the present specification.

As used herein, "siRNA" refers to an RNA molecule having a double-stranded RNA moiety consisting of 15 to 40 bases. A siRNA has a function of cleaving an mRNA of a target gene having a sequence complementary to an antisense strand of said siRNA to suppress the expression of the target gene. More specifically, the siRNA according to the present invention is an RNA comprising a double-stranded RNA moiety consisting of a sense RNA chain consisting of a sequence homologous to a contiguous RNA sequence in an mRNA of TGF-β or the like, and an antisense RNA chain consisting of a sequence complementary to the sense RNA sequence. The manufacturing and designing of the siRNA and mutant siRNA described below are within the scope of the ability of those skilled in the art. The concept of selecting any contiguous RNA region of an mRNA, which is a transcription product of a sequence of TGF-β or the like, and creating a double-stranded RNA corresponding to the region is merely a matter within the normal creative ability of those skilled in the art. Further, a siRNA sequence with a more potent RNAi effect from an mRNA sequence, which is a transcription product of the sequence, can be appropriately selected by those skilled in the art using a known method. Further, if one of the strands is identified, those skilled in the art can readily determine the base sequence of the other strand (complementary strand). Those skilled in the art can appropriately create a siRNA using a commercially available nucleic acid synthesizer. Further, a common synthesis service can be utilized for desired RNA synthesis.

The length of a double-stranded RNA moiety, as a base, is 15 to 40 bases, preferably 15 to 30 bases, more preferably 15 to 25 bases, still more preferably 18 to 23 bases, and most preferably 19 to 21 bases. It is understood that the upper and lower limits thereof are not limited to the specified limits where the limits can be any combinations of the mentioned limits. The terminal structure of a sense strand or antisense strand of a siRNA is not particular limited, which can be appropriately selected depending on the objective. For example, the terminal structure may have a smooth terminal or a protruding terminal (overhang), while a protruding 3' terminal is preferable. A siRNA having an overhang consisting of several bases, preferably 1 to 3 bases, and still more preferably 2 bases at the 3' terminal of a sense RNA strand and antisense RNA strand often is preferred for having a large effect of suppressing the expression of a target gene. The overhang base type is not particularly limited, which can be either a base constituting an RNA or a base constituting a DNA. Preferable overhang sequences include dTdT (2 bp of deoxy T) at the 3' terminal and the like. Examples of preferred siRNAs include, but are not limited to, those with dTdT (2 bp of deoxy T) added to the 3' terminal of sense and antisense strands of all siRNAs.

Furthermore, it is also possible to use a siRNA in which one to several nucleotides are deleted, substituted, inserted and/or added in either or both of the sense strand and antisense strand of the above-described siRNA. In this regard, the concept of one to several bases is not particularly limited, but is preferably 1 to 4 bases, still more preferably 1 to 3 bases, and most preferably 1 to 2 bases. Specific examples of such a mutation include, but are not limited to, mutations in which the number of bases at the 3' overhang moiety is from 0 to 3, mutations in which the base sequence of the 3'-overhang moiety is changed to another base sequence, mutations in which the lengths of the above-described sense RNA strand and antisense RNA strand are different by 1 to 3 bases due to an insertion, addition or deletion of bases, mutations in which the base in a sense strand and/or antisense strand is substituted with another base, and the like. However, it is necessary for the sense strand and the antisense strand to be able to hybridize in such mutant siRNAs, and for such mutant siRNAs to have the same ability to suppress gene expression as a siRNA that does not have a mutation.

Furthermore, a siRNA may be a molecule in which one end has a closed structure such as a siRNA with a hairpin structure (Short Hairpin RNA; shRNA). A shRNA is an RNA comprising a sense strand RNA of a specific sequence of a target gene, an antisense strand RNA consisting of a sequence complementary to the sense strand sequence, and a linker sequence connecting the two strands, wherein the sense strand moiety and the antisense strand moiety hybridize to form a double-stranded RNA moiety It is desirable that a siRNA does not exhibit the so-called off-target effect in clinical use. An off-target effect refers to an effect of suppressing the expression of another gene partially homologous to the siRNA used, other than the target gene. It is possible to confirm that a candidate siRNA does not have cross reactivity using a DNA microarray or the like in advance in order to avoid an off-target effect. Further, it is possible to avoid an off-target effect by confirming whether there is a gene comprising a moiety that is highly homologous to a sequence of a candidate siRNA, other than a target gene, using a known database provided by the NCBI (National Center for Biotechnology Information) or the like.

In order to create the siRNA according to the present invention, a known method, such as a method using chemical synthesis or a method using a gene recombination technique, can be appropriately used. With a method using synthesis, a double-stranded RNA can be synthesized based on sequence information by using a common method. With method using a gene recombination technique, a siRNA can be made by constructing an expression vector encoding a sense strand sequence or an antisense strand sequence and introducing the vector into a host cell, and then obtaining each of sense strand RNA and antisense strand RNA produced by transcription. Further, it is possible to create a desired double-stranded RNA by expressing a shRNA forming a hairpin structure, which comprises a sense strand of a specific sequence of a target gene, an antisense strand consisting of a sequence complementary to the sense strand sequence, and a linker sequence for linking the two strands.

For a siRNA, all or part of the nucleic acid constituting the siRNA may be a natural or a modified nucleic acid as long as such a nucleic acid has an activity to suppress the expression of a target gene.

The siRNA according to the present invention does not necessarily have to be a pair of double-stranded RNAs to a target sequence. It may be a mixture of a plurality of pairs (the "plurality" is not particularly limited, but preferably refers to a small number of about 2 to 5) of double-stranded RNAs to a region comprising a target sequence. In this regard, those skilled in the art can appropriately create a siRNA as a nucleic acid mixture corresponding to a target sequence by using a commercially available nucleic acid synthesizer and a DICER enzyme. Further, a common synthesis service can be utilized for desired RNA synthesis. It should be noted that the siRNA according to the present invention encompasses the so-called "cocktail siRNA". For the siRNA according to the present invention, not all the nucleotides have to be a ribonucleotide (RNA). Specifically, in the present invention, one or plurality of ribonucleotides constituting a siRNA may be a corresponding deoxyribonucleotide. The term "corresponding" refers to having the same base type (adenine, guanine, cytosine, thymine (uracil)) but a different sugar moiety structure. For example, a deoxyribonucleotide corresponding to a ribonucleotide having adenine refers to a deoxyribonucleotide having adenine.

Furthermore, a DNA (vector) which can express the above-described RNA according to the present invention is also encompassed as a preferred embodiment of a nucleic acid which can suppress expression of TGF-β or the like. For example, the DNA (vector) which can express the above-described double-stranded RNA according to the present invention is a DNA having a structure in which a DNA encoding one of the strands of the double-stranded RNA and a DNA encoding the other strand of the double-stranded RNA are linked with a promoter so that each of the DNAs can be expressed. The above-described DNA according to the present invention can be appropriately made by those skilled in the art using a common genetic engineering technique. More specifically, the expression vector according to the present invention can be made by appropriately inserting the DNA encoding an RNA according to the present invention into various known expression vectors.

In the present invention, a modified nucleic acid may be used as a nucleic acid for suppressing the expression of a target gene. A modified nucleic acid refers to a nucleic acid, which has a modification at a nucleoside (base moiety, sugar moiety) and/or an inter-nucleoside binding site, and has a structure different from that of a natural nucleic acid. Examples of "modified nucleoside", which constitutes a modified nucleic acid, include: an abasic nucleoside; arabinonucleoside, 2'-deoxyuridine, α-deoxyribonucleoside, β-L-deoxyribonucleoside, and nucleoside having other sugar modification; peptide nucleic acid (PNA), phosphate group-binding peptide nucleic acid (PHONA), locked nucleic acid (LNA), morpholino nucleic acid and the like. The above-described nucleosides having a sugar modification include 2'-O-methylribose, 2'-deoxy-2'-fluororibose, 3'-O-methylribose and other substituted pentose; 1',2'-deoxyribose; arabinose; substituted arabinose sugar; and nucleoside having a sugar modification of alpha-anomer and hexose. These nucleosides may be a modified base in which the base moiety is modified. Examples of such modified bases include 5-hydroxycytosine, 5-fluorouracil, 4-thiouracil and other pyrimidine; 6-methyladenine, 6-thioguanosine and other purine; and other heterocyclic bases.

Examples of a "modified inter-nucleoside bond", which constitutes a modified nucleic acid, include non-natural inter-nucleoside bonds, such as alkyl linker, glyceryl linker, amino linker, poly(ethylene glycol) bond, inter-methyl phosphonate nucleoside bond; methylphosphonothioate, phosphotriester, phosphothiotriester, phosphorothioate, phosphorodithioate, triester prodrug, sulfone, sulfonamide, sulfamate, formacetal, N-methylhydroxylamine, carbonate, carbamate, morpholino, boranophosphonate, phosphoramidate and the like.

The nucleic acid sequence comprised in the double-stranded siRNA according to the present invention includes a siRNA directed to TGF-β or other TGF-β signaling members, and the like.

It is also possible to introduce the nucleic acid or agent according to the present invention into a phospholipid endoplasmic reticulum (vesicle) such as a liposome to administer the endoplasmic reticulum. An endoplasmic reticulum in which a siRNA or shRNA is retained can be introduced into a predetermined cell using lipofection. The resulting cell is then systemically-administered, for example intravenously, intra-arterially or the like. The endoplasmic reticulum can also be locally administered to a required site in an eye or the like. While a siRNA exhibits a very good specific, post-transcription suppressing effect in vitro, the siRNA is quickly degraded in vivo due to nuclease activity in the serum. Since the duration thereof is limited, there has been a need for development of a better and more effective delivery system. As an example, Ochiya, T et al., Nature Med., 5:707-710, 1999, Curr. Gene Ther., 1: 31-52, 2001 reports that a biocompatible material atelocollagen, when mixed with a nucleic acid to form a complex, is a carrier having an action of protecting a nucleic acid from a degrading enzyme in a living organism and is extremely suitable as a carrier of a siRNA. While such a form can be used, the method for introducing a nucleic acid or medicament according to the present invention is not limited to this method. In this manner, due to fast degradation by the action of a nucleic acid degrading enzyme in serum in a living organism, it becomes possible to achieve continuation of the effect for an extended period of time. For example, Takeshita F. PNAS, (2003) 102 (34) 12177-82, Minakuchi Y Nucleic Acids Research (2004) 32 (13) e109 reports that atelocollagen derived from bovine skin forms a complex with a nucleic acid, which has action of protecting a nucleic acid from a degrading enzyme in a living organism and is extremely suitable as a carrier of a siRNA. Such a technique can be used.

As used herein, an "agent" is used in a broad sense, and may refer to any substance or other elements, (e.g., energy such as light, radiation, heat, and electricity) as long as the intended objective can be attained. Examples of such a substance include, but are not limited to, proteins, polypeptides, oligopeptides, peptides, polynucleotides, oligonucleotides, nucleotides, nucleic acids (e.g., including DNAs such as cDNA and genomic DNA, and RNAs such as mRNA), polysaccharides, oligosaccharides, fats, organic small molecules (e.g., hormones, ligands, information transmitting substances, organic small molecules, molecules synthesized by combinatorial chemistry, small molecules which can be utilized as a medicine (e.g., a low molecular weight ligand) and the like), and composite molecule thereof. Representative examples of an agent specific to a polynucleotide include, but are not limited to, a polynucleotide having complementarity with certain sequence homology (e.g., 70% or more sequence identity) relative to the sequence of the polynucleotide, a polypeptide such as a transcription factor binding to a promoter region, and the like. Representative examples of an agent specific to a polypeptide include, but are not limited to, an antibody specifically directed to the polypeptide or a derivative or an analog thereof (e.g., single-stranded antibody), a specific ligand or receptor when the polypeptide is a receptor or a ligand, a substrate when the polypeptide is an enzyme, and the like.

As used herein, "disease, disorder or condition associated with endoplasmic reticulum (ER) stress" in "corneal endothelium" refers to a disease, disorder or condition of a corneal endothelium, which is associated with endoplasmic reticulum (ER) stress.

As used herein, "disease, disorder or condition associated with endoplasmic reticulum (ER) associated stress" with respect to corneal endothelia includes any disease, disorder or condition associated with ER associated stress. Examples thereof include, but are not limited to, decreased corneal endothelial density, guttae formation, hypertrophy of the Descemet's membrane, hypertrophy of a cornea, corneal epithelial disorder, turbidity in corneal stroma, photophobia, blurred vision, visual impairment, ophthalmalgia, epiphora, hyperemia, pain, bullous keratopathy, eye discomfort, diminished contrast, glare, edema of the corneal stroma and the like. ER stress and mitochondrial disorder generally coexist, while all symptoms are generally manifested due to the mitochondrial disorder. Thus, the association therebetween can be detected or diagnosed by confirming mitochondrial failure. Further, many of the diseases, disorders and conditions are associated with apoptosis due to mitochondrial failure, they can also be detected or diagnosed by conforming apoptosis.

As used herein, "therapeutic agent for mitochondrial disorder (due to ER stress)" refers to a therapeutic agent that is substantially similar to an ER stress therapeutic drug. Examples thereof include, but are not limited to, BiP inducer X (BIX), 4-phenyl butyric acid (PBA), trimethylamine N-oxide (TMAO), tauroursodeoxycholic acid (TUDCA), teprenone (also sold as selbex) and the like (for example, see Journal of the Japanese Society of Psychiatry and Neurology (2012) Vol 114 No 2 p. 115).

As used herein, a "disease, disorder or condition related to Fuchs' endothelial corneal dystrophy" refers to any disease, disorder or condition related to Fuchs' endothelial corneal disorder, among which those associated with endoplasmic reticulum (ER) stress is of particular interest to the present invention, but are not limited thereto. Conceivable examples of such a disease, disorder or condition related to Fuchs' endothelial corneal dystrophy associated with endoplasmic reticulum (ER) stress includes those associated with a corneal endothelial cell disorder. Alternatively, examples of other forms of disease, disorder or condition related to Fuchs' endothelial corneal dystrophy include, but are not limited to, decreased corneal endothelial density, guttae formation, hypertrophy of the Descemet's membrane, hypertrophy of a cornea, corneal epithelial disorder, turbidity in corneal stroma, photophobia, blurred vision, visual impairment, ophthalmalgia, epiphora, hyperemia, pain, bullous keratopathy, eye discomfort, diminished contrast, glare, edema of the corneal stroma and the like. Fuchs' endothelial corneal dystrophy is a disease causing abnormality in endothelial cells inside the cornea, resulting in edema of the corneal stroma. The cause thereof is unknown. In Fuchs' endothelial corneal dystrophy, extracellular matrix such as collagen is deposited on a part of the back surface of a Descemet's membrane at the back of the cornea, resulting in hypertrophy of a corneal guttae and Descemet's membrane. Hypertrophy of the corneal guttae and Descemet's membrane is a cause of photophobia or blurred vision, which compromises the QOL of Fuchs' endothelial corneal dystrophy patients. It is understood that there is no effective therapeutic method other than corneal transplantation for Fuchs' endothelial corneal dystrophy. However, there is a shortage in cornea donation in Japan, where patients waiting for corneal transplantation is about 2600 whereas the number of corneal transplantation performed in Japan is about 1700 annually.

There are reports of immobilization (Azizi B, et al. Invest Ophthalmol Vis Sci. 2; 52(13): 9291-9297.2011) and culture of corneal endothelia cells from Fuchs' cornea patients (Zaniolo K, et al. Exp Eye Res.; 94(1): 22-31.2012 and Kelliher C. et al. Exp Eye Res Vol. 93 (6), 880-888, 2011). However, there is no report of cells suitable for screening a therapeutic drug or progression preventing drug retaining the features of a disease such as excessive production of extracellular matrix. Thus, development of a therapeutic drug thereof is limited, and there is no therapeutic drug that is currently in clinical use. Hence, there is no choice but to rely on corneal transplantation.

(General Technologies)

The molecular biological technology, biochemical technology, and microbiological technology as used herein are well known and commonly used in the art, They are described in, for example, Sambrook J. et al. (1989). Molecular Cloning: A Laboratory Manual, Cold Spring Harbor and 3rd Ed. thereof (2001); Ausubel, F. M. (1987). Current Protocols in Molecular Biology, Greene Pub. Associates and Wiley-Interscience; Ausubel, F. M. (1989). Short Protocols in Molecular Biology: A Compendium of Methods from Current Protocols in Molecular Biology, Greene Pub. Associates and Wiley-Interscience; Innis, M. A. (1990). PCR Protocols: A Guide to Methods and Applications, Academic Press; Ausubel, F. M. (1992). Short Protocols in Molecular Biology: A Compendium of Methods from Current Protocols in Molecular Biology, Greene Pub. Associates; Ausubel, F. M. (1995). Short Protocols in Molecular Biology: A Compendium of Methods from Current Protocols in Molecular Biology, Greene Pub. Associates; Innis, M. A. et al. (1995). PCR Strategies, Academic Press; Ausubel, F. M. (1999). Short Protocols in Molecular Biology: A Compendium of Methods from Current Protocols in Molecular Biology, Wiley, and annual updates; Sninsky, J. J. et al. (1999). PCR Applications: Protocols for Functional Genomics, Academic Press, Gait, M. J. (1985). Oligonucleotide Synthesis: A Practical Approach, IRL Press; Gait, M. J. (1990). Oligonucleotide Synthesis: A Practical Approach, IRL Press; Eckstein, F. (1991). Oligonucleotides and Analogues: A Practical Approach, IRL Press; Adams, R. L. et al. (1992). The Biochemistry of the Nucleic Acids, Chapman & Hall; Shabarova, Z. et al. (1994). Advanced Organic Chemistry of Nucleic Acids, Weinheim; Blackburn, G. M. et al. (1996). Nucleic Acids in Chemistry and Biology, Oxford University Press; Hermanson, G. T. (1996). Bioconjugate Techniques, Academic Press, Jikken Igaku Bessatsu [*Experimental Medicine, Separate Volume*], "Idenshi Dounyu & Hatsugen Kaiseki Jikkenho [Method of Gene Introduction & Expression Analysis Experimental Technique" Yodosha Co., Ltd., 1997, and the like. With regard to corneal endothelial cells, the reports from Nancy Joyce et al., {Joyce, 2004 #161} {Joyce, 2003 #7} are well known, while researches for effective culturing methods are currently ongoing by conducting transformation in a fibroblast-like manner through long-term culturing and subculturing as discussed above. The relevant portions (which may be all the portions) thereof are incorporated herein by reference.

DESCRIPTION OF PREFERRED EMBODIMENT

Hereinafter, preferred embodiments are described. However, it should be understood that the embodiments are exemplification of the present invention and the scope of the present invention is not limited to such preferred embodiments. It should also be understood that those skilled in the art can readily apply an alteration, change or the like within the scope of the present invention while referring to the following preferable Examples. The embodiments may appropriately combine any embodiments.

(Treatment or Prevention of Disease, Disorder or Condition Associated with Endoplasmic Reticulum (ER) Stress of Corneal Endothelium, Including TGFβ Signal Inhibitor)

In one aspect, the present invention provides a therapeutic or prophylactic drug for a disease, disorder or condition associated with ER stress in a corneal endothelium, comprising a TGFβ signal inhibitor. The present invention has found that ER stress can be unexpectedly reduced or eliminated, or maintained or returned to a normal level by administration of a TGFβ signal inhibitor for a disease, disorder or condition associated with ER stress in a corneal endothelium. Thus, such application of TGFββ signal inhibitor for treating or preventing a disease, disorder or condition associated with ER stress of a corneal endothelium is recognized as an application that was unexpected from conventional knowledge.

In a preferred embodiment, a target disease, disorder or condition of the present invention is a disorder related to Fuchs' endothelial corneal dystrophy. There is currently no fundamental therapeutic method of technique for Fuchs' endothelial corneal dystrophy such that therapy for Fuchs' endothelial corneal dystrophy is reliant on corneal transplantation. Since the present invention can treat ER stress, which is one of the important causes of abnormality or disorder in Fuchs' endothelial corneal dystrophy, it is understood that the present invention is useful in treating or preventing Fuchs' endothelial corneal dystrophy. ER stress in particular was found to be closely associated with apoptosis. Thus, there is expectation for the present invention to be a fundamental therapy for Fuchs' endothelial corneal dystrophy. The present invention can treat or prevent disorders of corneal endothelial cells in Fuchs' endothelial corneal dystrophy, as well as decreased corneal endothelial density, guttae formation, hypertrophy of the Descemet's membrane, hypertrophy of a cornea, corneal epithelial disorder, turbidity in corneal stroma, photophobia, blurred vision, visual impairment, ophthalmalgia, epiphora, hyperemia, pain, bullous keratopathy, eye discomfort, diminished contrast, glare, edema of the corneal stroma and the like.

For Fuchs' endothelial corneal dystrophy, the following is also confirmed with regard to TGF-β induced endoplasmic reticulum (ER) stress in corneal endothelial cells. Specifically, when normal donor cornea HCEC (iHCEC) and immobilized cell model (iFECD) of human patient corneal endothelial cells (HCEC) with Fuchs' endothelial corneal dystrophy (FECD) established by the inventors were used to investigate the involvement of ER stress in FECD of TGFβ signaling, involvement was demonstrated. It is also demonstrated that ER stress may be involved in cell loss in FECD. Thus, it is understood that inhibition of a TGFβ signaling pathway is demonstrated to be a possible effective therapy of FECD.

When iFECD and iHCEC were assessed with a transmission electron microscope (TEM) to elucidate the morphological change in ER in the present invention for Fuchs' endothelial corneal dystrophy, cell expansion was observed in iFECD, but not in iHCEC. Expression of ER stress sensors (PERK and ATF6) was stimulated with or without TGFβ and analyzed by Western blotting, and extracellular matrix protein production and ER colocalization were tested with immunostaining of type I and IV collagen, fibronectin and ER marker protein PDI, type I and IV collagen and fibronectin were observed to be highly expressed in iFECD than in iHCEC, but was found to be colocalized with ER. Further, it is known as the knowledge of the inventors that PERK phosphorylation and ATF6 cleavage were increased more in iFECD than in iHCEC by TGFβ. In order to investigate the involvement of TGFβ signaling in apoptosis, cells were treated with TGFβ and annexin V positive apoptosis cells were assessed by flow cytometry. The percentage of annexin V positive apoptosis cells in iHCEC did not increase relative to that prior to a TGF stimulation (as an exemplary data, 11.1±0.6% before stimulation and 12.3±0.5% after stimulation). Meanwhile, it is known that TGFβ increases annexin V positive cells after a stimulation in iFECD relative to the number prior to a TGFβ stimulation (as exemplary data, 19.4±1.4% prior to stimulation and 29.9±1.5% after stimulation, p<0.01). In addition thereto, it is shown that expression of the chaperone GRP78 is elevated. Further, it is shown that the expression of CHOP is elevated and apoptosis is induced by ER stress. Such promotion of phosphorylation and expression is more prominently observed in iFECD relative to iHCEC. It is shown that the increase can be seen after 3 hours and the effect of such increase is enhanced after 6 hours. Thus, it is demonstrated to increase with time.

Further, in one specific embodiment in the present invention, mitochondrial failure is shown to be involved with the level of functioning of corneal endothelial cells with Fuchs' endothelial corneal dystrophy. As demonstrated in the Examples, involvement of mitochondrial failure in FECD is demonstrated by using a cell model of normal donor cornea HCEC (iHCEC) and immobilized cell model of human corneal endothelial cells (HCEC) of FECD patients (iFECD).

For FECD, mitochondria expansion was observed in iFECD, but mitochondria in iHCEC are morphologically normal as in the assessment of iFECD and iHCEC with a transmission electron microscope (TEM). Thus, it was demonstrated that mitochondria become morphologically abnormal in Fuchs' endothelial corneal dystrophy. In addition, mitochondrial membrane potential (MMP) is shown to be lower in iFECD than in iHCEC as shown by JC-1 dye, MitoTracker®, and the like. Leakage of cytochrome c from mitochondria to cytoplasm is also shown to be higher in iFECD than in iHCEC with respect to the level of cytochrome c in a mitochondrial fraction as assessed by Western blot. As is shown by Western blot, caspase 9, caspase 3 and poly(ADP-ribose) polymerase (PARD) are observed to be cleaved by a mitochondrial stress stimulant (e.g., staurosporine). Thus, it is shown that mitochondrial failure is involved in apoptosis. It is known that ER stress induces a mitochondrial disorder in many cells. Thus, it is ready inferred that a mitochondrial disorder can be alleviated by controlling ER stress. In this manner, those skilled in the art can assess from the results of the present invention that mitochondrial failure is involved in the pathology of FECD and can be used as a target of a potent therapeutic agent.

Targets of administration (transplantation) of the medicament or method of the present invention include mammals (e.g., humans, mice, rats, hamsters, rabbits, cats, dogs, cows, horses, sheep, monkeys and the like). However, primates are preferred and humans are especially preferred. Satisfactory results have not been attained by corneal endothelial therapy in primates up to this point. In view of the above, the present invention provides an innovative therapeutic method and medicament.

TGF-β signaling pathways are roughly classified into Smad2/3 systems through ALK4, 5 or 7 and Smad1/5/8 systems through ALK1, 2, 3, or 6, which are all well known to be associated with fibrosis (J. Massagu'e, Annu. Rev. Biochem. 1998.67: 753-91; Viler J M G, Jansen R, Sander C (2006) PLoS Comput Biol 2(1): e3; Leask, A., Abraham, D. J. FASEB J. 18, 816-827 (2004); Coert Margadant & Arnoud Sonnenberg EMBO reports (2010) 11, 97-105; Joel Rosenbloom et al., Ann Intern Med. 2010; 152:159-166.) It is known that BMP-7 can suppress TGF-β signals to suppress fibrosis (In addition to the above-described documents, Ralf Weiskirchen, et al., Frontiers in Bioscience 14, 4992-5012, Jun. 1, 2009; Elisabeth M Zeisberg et al., Nature Medicine 13, 952-961 (2007); Michael Zeisberg et al., Nature Medicine 9, 964-968(2003)). Although these documents describe involvement of TGF-β in conditions actually accompanied by membranous tissue consisting of extracellular matrix such as collagen due to an artificially made severe disorder or a rare disease, syphilitic interstitial keratitis, it is difficult to predict the therapeutic effect therefrom. Further, it is also shown that fibrosis upon a severe disorder of a cornea is due to activation of p38 MAPK during fibrosis by IL-1β. Meanwhile, it is shown with rabbits that fibrosis observed when suffering from severe inflammation in a living organism due to excessive freeze injury in rabbits is accompanied by p38 MAPK activation and fibrosis can be partially suppressed with an inhibitor. Such knowledge shows that p38 MAPK activation is accompanied in a situation where a living organism has very strong inflammation and membranous tissue consisting of extracellular matrix is accompanied. Such knowledge does not show that a TGF-β signal inhibitor is effective for the treatment or prevention of a disease, disorder or condition associated with ER stress on corneal endothelia (e.g., disorder such as Fuchs' endothelial corneal dystrophy), or provide any suggestion regarding maintenance of a normal condition. In this manner, it has been considered difficult to culture corneal endothelial cells while maintaining normal functioning. Previously reported knowledge ultimately could not treat or prevent a disease, disorder or condition associated with ER stress in a corneal endothelium such as Fuchs' endothelial corneal dystrophy. Suppression of a TGF-β signaling pathway to treat or prevent a disease, disorder or condition associated with ER stress in a corneal endothelium (e.g., disorder such as Fuchs' endothelial corneal dystrophy) was not even considered possible.

Any agent may be used as the TGF-β signal inhibitor used in the present invention, as long as a TGF-β signal pathway can be inhibited. Further, as is well known, a TGF-β signaling pathway to be inhibited may be a factor associated with any signal as long as an effect similar to (complete opposite for inhibitors, antagonists or the like) that for a TGF-β signaling pathway is ultimately exerted as in BMP-7, in addition to factors to which TGF-β and TGF-β receptors are directly associated.

The present invention can comprise a single TGF-β signal inhibitor alone or use and comprise several types thereof as needed.

In one embodiment, a TGF-β signal inhibiting agent comprises at least one of an antagonist of TGF-β, an antagonist of a TGF-β receptor or an inhibitor of Smad3, other ingredients exemplified in the present specification, a pharmaceutically acceptable salt or a solvate thereof, or a solvate of a pharmaceutically acceptable salt thereof. Any inhibitor thereof described in other parts of the present specification can be used as the inhibitor of antagonist of TGF-β, the antagonist of a receptor of TGF-β, and the inhibitor of Smad3.

In one embodiment, the TGF-β signal inhibitor which can be used in the present invention comprises at least one of SB431542 (4-[4-(1,3-benzodioxole-5-yl)-5-(2-pyridinyl)-1H-imidazole-2-yl]benzamide), BMP-7, anti-TGF-β antibody, anti-TGF-β receptor antibody, siRNA of TGF-β, siRNA of a TGF-β receptor, antisense oligonucleotide of TGF-β, 6,7-dimethoxy-2-((2E)-3-(1-methyl-2-phenyl-1H-pyrrolo[2,3-b] pyridine-3-yl-prop-2-enoyl))-1,2,3,4-tetrahydroisoquinolone, A83-01 (3-(6-methyl-2-pyridinyl)-N-phenyl-4-(4-quinolinyl)-1H-pyrazole-1-carbothioamide), Stemolecule™ TLK inhibitor (2-(3-(6-methylpyridine-2-yl)-1H-pyrazole-4-yl)-1,5-naphthyridine), Stemolecule™ BMP inhibitor LDN-193189 (6-(4-(piperidine-1-yl)ethoxy) phenyl)-3-(pyridine-4-yl) pyrazolo[1,5-a]pyrimidine), SD-208 (2-(5-chloro-2-fluorophenyl)-4-[(4-pyridinyl) amino]pteridine), LY364947 (4-[3-(2-pyridinyl)-1H-pyrazole-4-yl]-quinoline), other ingredients exemplified in the present specification, a pharmaceutically acceptable salt or a solvate thereof, or a solvate of a pharmaceutically acceptable salt thereof. The mentioned antibodies may be a neutralizing antibody, but are not limited thereto. Although not wishing to be bound by any theory, it is understood that the effect of the present invention can be achieved by a TGF-β signal inhibitor of any of these pathways. The effect of the ALK-4, 5, and 7 inhibitor A83-01 (3-(6-methyl-2-pyridinyl)-N-phenyl-4-(4-quinolinyl)-1H-pyrazole-1-carbothioamide) is also demonstrated in the Examples. Thus, it is understood that an ALK-4, 5, 7 inhibitor can also be used in the specific Examples of the present invention. In addition, the effect of the ALK-5 inhibitor 2-(3-(6-methylpyridine-2-yl)-1H-pyrazole-4-yl)-1,5-naphthyridine is also demonstrated in the Examples. Thus, it is understood that an ALK-5 inhibitor can also be used in the specific Examples of the present invention.

In a preferred embodiment, the TGF-β signal inhibiting agent used in the present invention comprises SB431542 (4-[4-(1,3-benzodioxole-5-yl)2-pyridinyl)-1H-imidazole-2-yl]benzamide). This is because it was shown that a disease, disorder or condition associated with ER stress in a corneal endothelium (e.g., disorder related to Fuchs' endothelial corneal dystrophy or the like) is ameliorated. In a preferred embodiment, SB431542 is comprised to be present at a concentration of about 0.1 µM to about 10 µM in use, preferably at a concentration of about 1 µM to about 10 µM in use, and still more preferably at a concentration of about 1 µM in use.

The concentration of the TGF-β signal inhibitor used in the present invention is generally about 0.1 to 100 µmol/l, preferably about 0.1 to 30 µmol/l, and more preferably about 1 µmol/l. When several types thereof are used, the concentration may be changed appropriately. Examples of other concentration ranges include, but not limited to, generally about 0.001 to 100 µmol/l, preferably about 0.01 to 75 µmol/l, about 0.05 to 50 µmol/l, about 1 to 10 µmol/l, about 0.01 to 10 µmol/l, about 0.05 to 10 µmol/l, about 0.075 to 10 µmol/l, about 0.1 to 10 µmol/l, about 0.5 to 10 µmol/l, about 0.75 to 10 µmol/l, about 1.0 to 10 µmol/l, about 1.25 to 10 µmol/l, about 1.5 to 10 µmol/l, about 1.75 to 10 µmol/l, about 2.0 to 10 µmol/l, about 2.5 to 10 µmol/l, about 3.0 to 10 µmol/l, about 4.0 to 10 µmol/l, about 5.0 to 10 µmol/l, about 6.0 to 10 µmol/l, about 7.0 to 10 µmol/l, about 8.0 to 10 µmol/l, about 9.0 to 10 µmol/l, about 0.01 to 50 µmol/l, about 0.05 to 5.0 µmol/l, about 0.075 to 5.0 µmol/l, about 0.1 to 5.0 µmol/l, about 0.5 to 5.0 µmol/l, about 0.75 to 5.0 µmol/l, about 1.0 to 5.0 µmol/l, about 1.25 to 5.0 µmol/l, about 1.5 to 5.0 µmol/l, about 1.75 to 5.0 µmol/l, about 2.0 to 5.0 µmol/l, about 2.5 to 5.0 µmol/l, about 3.0 to 5.0 µmol/l, about 4.0 to 5.0 µmol/l, about 0.01 to 3.0 µmol/l, about 0.05 to 3.0 µmol/l, about 0.075 to 3.0 µmol/l, about 0.1 to 3.0 µmol/l, about 0.5 to 3.0 µmol/l, about 0.75 to 3.0 µmol/l, about 1.0 to 3.0 µmol/l, about 1.25 to 3.0 µmol/l, about 1.5 to 3.0 µmol/l, about 1.75 to 3.0 µmol/l, about 2.0 to 3.0 µmol/l, about 0.01 to 1.0 µmol/l, about 0.05 to 1.0 µmol/l, about 0.075 to 1.0 µmol/l, about 0.1 to 1.0 µmol/l, about 0.5 to 1.0 µmol/l, about 0.75 to 1.0 µmol/l, about 0.09 to 35 µmol/l, about 0.09 to 3.2 µmol/l, and more preferably about 0.05 to 1.0 µmol/l, about 0.075 to 1.0 µmol/l, about 0.1 to 1.0 µmol/l, about 0.5 to 1.0 µmol/l, and about 0.75 to 1.0 µmol/l.

In a preferred embodiment, a TGF-β signal inhibitor that is used comprises 4-[4-(1,3-benzodioxole-5-yl)2-pyridinyl)-1H-imidazole-2-yl]benzamide or a pharmaceutically acceptable salt thereof.

In another preferred embodiment, the TGF-β signal inhibitor used in the present invention comprises BMP-7. This is because: fibrosis was suppressed; it was demonstrated that a protein in charge of normal functions was retained, and it can withstand transplantation into primates. In a preferred embodiment, BMP-7 is comprised to be present at a concentration of about 10 ng/ml to about 1,000 ng/ml in use, and more preferably at a concentration of about 100 ng/ml to about 1,000 ng/ml in use. BMP-7 may be comprised to be present at a concentration of about 100 ng/ml in use or at a concentration of about 1,000 ng/ml.

In one embodiment, a TGF-β signal inhibitor can treat mitochondrial failure. The treatment of mitochondrial failure may be, for example, for Fuchs' endothelial corneal dystrophy, but is not limited thereto.

Alternatively, an agent for treating mitochondrial failure can be used alone or with another agent such as a TGF-β signal inhibitor for ophthalmic therapy, especially corneal endothelial therapy. Examples of agents for treating a disease, disorder or condition associated with mitochondrial failure include, but are not limited to, vitamins used by a specific element of a mitochondrial respiratory chain (e.g., vitamin E or a derivative thereof), cofactors, coenzyme Q (ubiquitin), nicotinamide, riboflavin, carnitine, biotin, lipoic acid and the like.

Examples of diseases caused by mitochondrial failure may include mitochondrial swelling due to latent dysfunction of mitochondria, dysfunction due to oxidative stress (e.g., due to action of free radicals or reactive oxygen species), dysfunction due to a genetic factor, and diseases due to failure of oxidative phosphorylation mechanism for energy production of mitochondria. There are many specific examples of diseases that progress due to the above-described pathological factors, but those related to the ophthalmic field include, but are not limited to, optic atrophy, optic neuropathy, retinitis pigmentosa, and cataract. Further, as another form of the aforementioned disease, disorder or condition related to Fuchs' endothelial corneal dystrophy, decreased corneal endothelial density, guttae formation, hypertrophy of the Descemet's membrane, hypertrophy of a cornea, corneal epithelial disorder, turbidity in corneal stroma, photophobia, blurred vision, visual impairment, ophthalmalgia, epiphora, hyperemia, pain, bullous keratopathy, eye discomfort, diminished contrast, glare, edema of the corneal stroma and the like are also examples of a disease, disorder or condition associated with a corneal endothelium caused by mitochondrial failure.

The therapeutic or prophylactic drug of the present invention may comprise an additional pharmaceutical ingredient. Representative examples of such a pharmaceutical product include Rho kinase inhibitors, steroids and the like. Although not wishing to be bound by any theory, this is because since inclusion of a Rho kinase inhibitor allows prevention of cell loss by promoting adhesion of corneal endothelial cells and formation of a corneal endothelial cell layer with excellent cell morphology and high cellular density, the effect of a TGF-β signal inhibitor can be enhanced. The present invention can comprise one type of Rho kinase inhibitor alone or several types of Rho kinase inhibitors for combined use as needed.

Examples of Rho kinase inhibitors that can be used in the present invention include compounds disclosed in the following documents: U.S. Pat. No. 4,678,783, Japanese Patent No. 3421217, International Publication No. WO 95/28387, International Publication No. WO 99/20620, International Publication No. WO 99/61403, International Publication No. WO 02/076976, International Publication No. WO 02/076977, International Publication No. WO 2002/083175, International Publication No. WO 02/100833, International Publication No. WO 03/059913, International Publication No. WO 03/062227, International Publication No. WO 2004/009555, International Publication No. WO 2004/022541, International Publication No. WO 2004/108724, International Publication No. WO 2005/003101, International Publication No. WO 2005/039564, International Publication No. WO 2005/034866, International Publication No. WO 2005/037197, International Publication No. WO 2005/037198, International Publication No. WO 2005/035501, International Publication No. WO 2005/035503, International Publication No. WO 2005/035506, International Publication No. WO 2005/080394, International Publication No. WO 2005/103050, International Publication No. WO 2006/057270, International Publication No. WO 2007/026664 and the like. Each of such compounds can be manufactured by the methods described in the documents in which the respective compounds are disclosed. Examples include 1-(5-isoquinolinesulfonyl)homopiperazine or a salt thereof (e.g., fasudil (1-(5-isoquinolinesulfonyl)homopiperazine)), (R)-(+)-trans-(4-pyridyl)-4-(1-aminoethyl)-cyclohexanecarboxamide) or a salt thereof (e.g., Y-27632 ((R)-(+)-trans-(4-pyridyl)-4-(1-aminoethyl)-dihydrochloride cyclohexanecarboxamide monohydrate) and the like) and the like.

The concentration of the Rho kinase inhibitor in the present invention is generally about 1 to 100 µmol/l, preferably about 5 to 20 µmol/l, and more preferably about 10 µmol/l. When several types thereof are used, the concentration may be changed appropriately. Examples of other concentration ranges include, but are not limited to, generally about 0.001 to 100 µmol/l, preferably about 0.01 to 75 µmol/l, about 0.05 to 50 µmol/l, about 1 to 10 µmol/l, about 0.01 to 10 µmol/l, about 0.05 to 10 µmol/l, about 0.075 to 10 µmol/l, about 0.1 to 10 µmol/l, about 0.5 to 10 µmol/l, about 0.75 to 10 µmol/l, about 1.0 to 10 µmol/l, about 1.25 to 10 µmol/l, about 1.5 to 10 µmol/l, about 1.75 to 10 µmol/l, about 2.0 to 10 µmol/l, about 2.5 to 10 µmol/l, about 3.0 to 10 µmol/l, about 4.0 to 10 µmol/l, about 5.0 to 10 µmol/l, about 6.0 to 10 µmol/l, about 7.0 to 10 µmol/l, about 8.0 to 10 µmol/l, about 9.0 to 10 µmol/l, about 0.01 to 50 µmol/l, about 0.05 to 5.0 µmol/l, about 0.075 to 5.0 µmol/l, about 0.1 to 5.0 µmol/l, about 0.5 to 5.0 µmol/l, about 0.75 to 5.0 µmol/l, about 1.0 to 5.0 µmol/l, about 1.25 to 5.0 µmol/l, about 1.5 to 5.0 µmol/l, about 1.75 to 5.0 µmol/l, about 2.0 to 5.0 µmol/l, about 2.5 to 5.0 µmol/l, about 3.0 to 5.0 µmol/l, about 4.0 to 5.0 µmol/l, about 0.01 to 3.0 µmol/l, about 0.05 to 3.0 µmol/l, about 0.075 to 3.0 µmol/l, about 0.1 to 3.0 µmol/l, about 0.5 to 3.0 µmol/l, about 0.75 to 3.0 µmol/l, about 1.0 to 3.0 µmol/l, about 1.25 to 3.0 µmol/l, about 1.5 to 3.0 µmol/l, about 1.75 to 3.0 µmol/l, about 2.0 to 3.0 µmol/l, about 0.01 to 1.0 µmol/l, about 0.05 to 1.0 µmol/l, about 0.075 to 1.0 µmol/l, about 0.1 to 1.0 µmol/l, about 0.5 to 1.0

µmol/l, about 0.75 to 1.0 µmol/l, about 0.09 to 35 µmol/l, about 0.09 to 3.2 µmol/l, and more preferably about 0.05 to 1.0 µmol/l, about 0.075 to 1.0 µmol/l, about 0.1 to 1.0 µmol/l, about 0.5 to 1.0 µmol/l, and about 0.75 to 1.0 µmol/l.

The present invention can be administered as eye drops.

The dosage and dosing frequency vary depending on the symptom, age, weight, or dosing format. For example, when used as eye drops, a formulation containing about 0.0001-0.1 w/v % of effective ingredient, preferably about 0.003-0.03 w/v % can generally be administered 1-10 times a day, preferably 1-6 times, more preferably 1-3 times with about 0.01-0.1 mL per dose for adults. When the medicament of the present invention is injected into the anterior chamber, a formulation with a concentration that is ¹⁄₁₀ to ¹⁄₁₀₀₀ of the above-described concentration may be used. Those skilled in the art can appropriately select the type and concentration of TGFβ signal inhibitor, Rho kinase inhibitor or the like depending on the condition of the disease.

In another aspect, the present invention provides a TGFβ signal inhibiting substance for treating or preventing a disorder associated with ER stress of a corneal endothelium. A TGFβ signal inhibiting substance can be used interchangeably with a TGFβ signal inhibitor. Any embodiment explained herein can be used for corneal endothelial ER stress and TGF-β signal inhibitor.

In another aspect, the present invention provides a method of treating or preventing a disease, disorder or condition associated with ER stress in a corneal endothelium in a subject, wherein the method comprises a step of administering an effective amount of a TGF-β signal inhibitor to the subject. In this method, any embodiment explained herein can be used for the TGF-β signal inhibitor and disease, disorder or condition associated with ER stress of a corneal endothelium.

Targets of administration (transplantation) of the medicament or method of the present invention include mammals (e.g., humans, mice, rats, hamsters, rabbits, cats, dogs, cows, horses, sheep, monkeys and the like). However, primates are preferred and humans are especially preferred. Satisfactory results have not been attained by corneal endothelial therapy in primates up to this point. In view of the above, the present invention provides an innovative therapeutic method and medicament. The effective amount of therapeutic agent of the present invention that is effective in treating a specific disease, disorder or condition may vary depending on the characteristic of the disorder or condition. However, those skilled in the art can determine the effective amount by a standard clinical technique based on the description herein. Furthermore, use of an in vitro assay can assist in identifying the optimal range of dosage in some cases. Since the accurate dose to be used in a mixture can vary depending on the administration pathway or the severity of disease or disorder, the dose should be determined in accordance with the judgment of a physician or the condition of each patient. However, the dosage, although not particularly limited, may be for example, 0.001, 1, 5, 10, 15, 100, or 1000 mg/kg body weight per dose or within a range of any of the two values. The dosing interval is not particularly limited, but examples thereof may be 1 or 2 dose per 1, 7, 14, 21, or 28 days or 1 or 2 doses per a range between 2 of any of the values. The dosage, dosing interval, and dosing method may be appropriately selected depending on the age, weight, symptom, target organ or the like of a patient. Further, a therapeutic drug preferably comprises an effective ingredient in a therapeutically effective amount or in an effective amount that exerts a desired action. Presence of a therapeutic effect may be acknowledged when a therapeutic marker significantly decreases after administration. The effective dose can be estimated from a dose-response curve obtained from an in vitro or animal model testing system.

Reference literatures such as scientific literatures, patents, and patent applications cited herein are incorporated herein by reference to the same extent that the entirety of each document is specifically described.

As described above, the present invention has been disclosed by showing preferable embodiments to facilitate understanding. The present invention is disclosed below based on Examples. The aforementioned disclosure and the following Examples are not provided for the purpose of limiting the present invention, but for the sole purpose of exemplification. Thus, the scope of the present invention is not limited to embodiments and Examples specifically described herein and is limited only by the scope of claims.

EXAMPLES

Hereinafter, examples of the present invention are disclosed. Biological samples or the like, when applicable, were handled in compliance with the standards enacted by the Ministry of Health, Labour and Welfare, Ministry of Education, Culture, Sports, Science and Technology, or the like and, if applicable, based on the Helsinki Declaration or ethical codes prepared based thereon. For the donation of eyes used for the research, consent was obtained from close relatives of all the deceased donors. The present research was approved by the ethics committee or a corresponding body of the University of Erlangen and SightLife™ (Seattle, Wash.) eye bank.

Fuchs' endothelial corneal dystrophy leads to the death of corneal endothelial cells. When the remaining corneal endothelial cells cannot compensate for the lost pumping function or barrier function, transparency of a cornea cannot be maintained, resulting blindness due to corneal opacity. Further, corneal endothelial cells of a Fuchs' endothelial corneal dystrophy patient are known to produce excessive extracellular matrix, resulting in hypertrophy of Descemet's membrane and guttae formation. Guttae formation and hypertrophy of Descemet's membrane leads to light scattering or the like to cause reduced visual acuity, photophobia, or blurred vision to significantly compromise the QOL of a patient. Immobilized corneal endothelial cell lines (iFECD) from a Fuchs' endothelial corneal dystrophy patient was used as a model and compared to immobilized corneal endothelial cell lines (iHCEC) from a healthy donor to elucidate the cause of extracellular matrix production and to identify a therapeutic target.

Preparation Example 1: Production of Immobilized Corneal Endothelial Cell Line (iFECD) Model from Fuchs' Endothelial Corneal Dystrophy Patient In the present example, an immobilized corneal endothelial cell line (iFECD) was made from corneal endothelial cells from Fuchs' endothelial corneal dystrophy patients.

(Culture Method)

Corneal endothelial cells were mechanically peeled off with a basal membrane from a corneal for research purchased from the Seattle Eye Bank. After collagenase was used to detach and collect the corneal endothelial cell from the basal membrane, the cells were subjected to primary culture. For a medium, Opti-MEM I Reduced-Serum Medium, Liquid (INVITROGEN catalog No.: 31985-070) to which 8% FBS (BIOWEST, catalog No.: S1820-500), 200 mg/ml of $CaCl_2 \cdot 2H_2O$ (SIGMA catalog No.: C7902-500G), 0.08% of chondroitin sulfate (SIGMA catalog No.: C9819-5G), 20 µg/ml of ascorbic acid (SIGMA catalog No.: A4544-25G), 50 µg/ml of gentamicin (INVITROGEN catalog No.: 15710-064) and 5 ng/ml of EGF (INVITROGEN catalog No.: PHG0311) were added and acclimated for a 3T3 feeder cell was used as a basal medium. Further, the cells were cultured in a basal medium to which SB431524 (1 µmol/l) and SB203580 (4-(4-fluorophenyl)-2-(4-methylsulfonylphenyl)-5 (4-pyridyl) imidazole<4-[4-(4-fluorphenyl)-2-(4-methylsulfinylphenyl)-1H-imidazole-5-yl]pyridine) (1 µmol/l) were added (also referred to as "SB203580+SB431542+3T3 acclimated medium" herein).

(Method of Acquisition)

Corneal endothelial cells were obtained under approval from an ethics committee and written consent from 3 human patients who suffered from bullous keratopathy according to a clinical diagnosis of Fuchs' endothelial corneal dystrophy and underwent corneal endothelial transplantation (Descemet's Membrane Endothelial Keratoplasty=DMEK). For DMEK, pathological corneal endothelial cells were mechanically peeled off with Descemet's membrane, the basal membrane, and immersed in a cornea preserving solution Optisol-GS (Bauch & Lomb). Collagenase treatment was then applied to enzymatically collect the corneal endothelial cells and the cells were cultured with a SB203580+SB431542+3T3 acclimated medium. For cultured corneal endothelial cells from a Fuchs' endothelial corneal dystrophy patient, SV40 large T antigen and hTERT gene were amplified by PCR and introduced into a lentiviral vector (pLenti6.3_V5-TOPO; Life Technologies Inc). The lentiviral vector was then used to infect 293T cells (RCB2202; Riken Bioresource Center, Ibaraki, Japan) with a transfection reagent (Fugene H D; Promega Corp., Madison, Wis.) and three types of helper plasmids (pLP1, pLP2, pLP/VSVG; Life Technologies Inc.). Culture supernatant comprising viruses was collected after 48 hours from the infection. 5 µg/ml of polybrene was used and added to a culture solution of cultured corneal endothelial cells from a Fuchs' endothelial corneal dystrophy patient, and SV40 large T antigen and hTERT gene were introduced. Images of immobilized corneal endothelial cell line (iFECD) from Fuchs' endothelial corneal dystrophy patients from a phase difference microscope were studied. Corneal endothelial cells cultured from a research cornea imported from the Seattle Eye Bank were immobilized by the same method to make an immobilized cell line of normal corneal endothelial cells (iHCEC) as a control. When images of the immobilized corneal endothelial cell line (iFECD) and the immobilized corneal endothelial cell line from a healthy donor (iHCEC) from a phase difference microscope are studied, both iHCEC and iFECD have a layer of polygonal form as in normal corneal endothelial cells. IHCEC and iFECD were maintained and cultured with DMEM+10% FBS. SB431542 was obtained from TOCRIS (catalog number: 1614). SB203580 was obtained from CALBIOCHEM (catalog number: 559389).

Preparation Example 2: Confirmation of Normal Functioning of Immobilized Corneal Endothelial Cell Line (iFECD)

Normal functioning of an immobilized corneal endothelial cell line (iFECD) was confirmed in the present Example.

(Immunostaining by $Na^+/K^+$-ATPase and ZO-1)

First, immunostaining was performed with $Na^+/K^+$-ATPase and ZO-1 to confirm normal functioning of an immobilized corneal endothelial cell line (iFECD). This is for examining the functions of corneal endothelial cells, i.e., pumping and barrier functions. $Na^+/K^+$-ATPase and ZO-1 indicates normal pumping and barrier functions of corneal endothelial cells, respectively. The technology is as follows.

(Method of Observing Cells with Staining or the Like (Histological Test))

Cells were observed with a phase difference microscope. After cells were immobilized, immunostaining was applied with ZO-1 and $Na^+/K^+$-ATPase as function associated markers for observation with a fluorescent microscope. For a tissue staining test, cultured cells were placed in Lab-Tek™ Chamber Slides™ (NUNC A/S, Roskilde, Denmark), immobilized with 4% formaldehyde for 10 minutes at room temperature (RT), and incubated for 30 minutes with 1% bovine serum albumin (BSA). Specifically, cultured cells on Lab-Tek™ Chamber Slides™ (NUNC A/S, Roskilde, Denmark) were immobilized in 4% formaldehyde for 10 minutes at room temperature and incubated for 30 minutes with 1% bovine serum albumin (BSA). To investigate the phenotype of the cells, immunohistological chemical analysis was performed on ZO-1, which is a close bond associated protein and $Na^+/K^+$-ATPase, which is a pumping function associated protein. ZO-1 and $Na^+/K^+$-ATPase were used as markers associated with cell functions. ZO-1 and $Na^+/K^+$-ATPase were stained with a 1:200 dilution of ZO-1 polyclonal antibody (Zymed Laboratories, Inc., South San Francisco, Calif.) and $Na^+/K^+$-ATPase monoclonal antibody (Upstate Biotec, Inc., Lake Placid, N.Y.), respectively. For secondary antibodies, a 1:2000 dilution of Alexa Fluor® 488 labeling or Alexa Fluor® 594 labeling goat antimouse IgG (Life Technologies) was used. Cellular nuclei were then stained with DAPI (Vector Laboratories, Inc., Burlingame, Calif.) or PI (Sigma-Aldrich). Slides were then observed with a fluorescent microscope (TCS SP2 AOBS; Leica Microsystems, Welzlar, Germany).

When the results were studied, $Na^+/K^+$-ATPase and ZO-1 were expressed in all cells of iHCEC and iFECD, demonstrating that normal function is maintained in the produced immobilized cell line.

Further, images of morphological observation of iHCEC and iFECD from a transmission electron microscope were examined (data not shown). IHCEC and iFECD were cultured on a Transwell serum free with a DMEM and immobilized in a confluent state after a week, and the morphology was observed with a transmission electron microscope. It was demonstrated therefrom that iHCEC and iFECD were a layer of cells from which no obvious morphological abnormality were found.

Further, it is known that corneal endothelial cells of Fuchs' endothelial corneal dystrophy patients produce excessive extracellular matrix, leading to guttae formation and hypertrophy of Descemet's membrane. In this regard, for expression of type I collagen, type IV collagen, and fibronectin, which are constituent proteins of extracellular matrix, iHCEC and iFECD were cultured in a culture dish and immunostaining was performed thereon. It was demonstrated that expression of type I collagen, type IV collagen, and fibronectin increased in iFECD relative to iHCEC. Further, when gene expression levels of cultured iHCEC and iFECD were examined with real time PCR, significant elevation in expression levels of type I collagen and fibronectin was observed and tendency of elevated expression was observed for type IV collagen. Examinations were conducted as to whether iFECD produced excessive extracellular matrix as in corneal endothelia of Fuchs' endothelial corneal dystrophy patients. IHCEC and iFECD were cultured serum-free in a Transwell with a DMEM, immobilized in a confluent state after a week, and applied with HE staining. Production of extracellular matrix with significant hypertrophy was observed in iFECD relative to iHCEC. In view of the above, a disease model cell was made having a feature of producing excessive extracellular matrix in Fuchs' endothelial corneal dystrophy patients. Since it is expected that analysis using the disease model cells would contribute to elucidation of the pathology of Fuchs' endothelial corneal dystrophy with many unanswered questions, the cells were used below to attempt the development of a therapeutic drug for Fuchs' endothelial corneal dystrophy as a representative example of diseases associated with endoplasmic reticulum stress.

Example 1: Morphological Observation of Endoplasmic Reticulum and Mitochondria in Fuchs' Endothelial Corneal Dystrophy The present Example observed whether morphological abnormality is observed in endoplasmic reticulum and mitochondria in cells with Fuchs' endothelial corneal dystrophy model prepared in the above-described Preparation Example as a representative example in order to study endoplasmic reticulum stress.

(Observation of Organelles by Electron Microscope)

Cells were then observed with an electron microscope to confirm elevation in ECM production and ER stress. As a pre-immobilization, a transwell seeded with cells was immobilized for three hours at room temperature with 2.5% glutaraldehyde with a pH 7.2 diluted with 0.1 M sodium cacodylate and washed three times with 0.1 M sodium cacodylate. Then, as post immobilization, it was immobilized for 1 hour at room temperature with 1% osmic acid diluted with 0.1 M sodium cacodylate and washed three times with distilled water. In order to study the localization and morphological change of organelles, the cells were immersed for 1 hour in 0.5% uranyl acetate at room temperature. The cells were immersed for 10 minutes in each of 70% ethanol and 90% ethanol and immersed for 20 minutes in 100% ethanol for dehydration. The cells were then immersed in propylene oxide for 30 minutes and immersed for 1 hour at room temperature in a mixture of 1 part propylene oxide and 1 part araldite resin. The transwell was immersed in the araldite resin mixture and soaked for 2 hours at room temperature. The araldite resin mixture was exchanged every 2 hours three times. After 12 hours, the araldite resin was exchanged again every 2 hours three times. Subsequently, the cells were embedded in an araldite resin mixture, incubated for 24 hours at 60° C., and hardened. A microtome (Leica EMUC7, Leica Microsystems, Welzlar, Germany) was used to make a 300 nm section and collected onto a grid. After staining the grid, the section was observed with an electron microscope.

(Results)

The results are shown in FIG. 2. It was revealed that there is morphological abnormality in the endoplasmic reticulum and mitochondria in Fuchs' endothelial corneal dystrophy. More specifically, endoplasmic reticulum and mitochondria of normal form were observed in iHCEC, while extracellular matrix was not found. On the other hand, the endoplasmic reticulum and mitochondria expanded to exhibit morphological abnormality in iFECD. Further, extracellular matrix was found between cells.

In view of the results, endoplasmic reticulum and mitochondria were found to have morphological abnormality in a Fuchs' endothelial corneal dystrophy model.

Example 2: Elevation in Endoplasmic Reticulum Stress in Corneal Endothelial Cells in Fuchs' Endothelial Corneal Dystrophy The present Example observed expression of molecular chaperones GRP78 and GADD153 expressed in response to endoplasmic reticulum stress in order to examine whether endoplasmic reticulum stress is elevated in a Fuchs' endothelial corneal dystrophy model. GADD153 is known as a protein, which is expressed/elicited in response to a variety of stress, especially stress on the endoplasmic reticulum, discontinues a cell cycle, and is involved in apoptosis (As a reference document, see Verfaillie T, et al. Cancer Lett. 2013 May 28; 332(2): 249-64).

(Materials and Methods)

(Observation of Expression with Immunostaining)

Expression of GRP78 and GADD153 associated with ER stress was confirmed to be elevated by immunostaining. The method of immunostaining was in accordance with the above-described Preparation Example 2. The antibodies were changed to antibodies to GRP78 and GADD153 for the experiment.

Antibodies to GRP78: (sc-376768, SANTA CRUZ BIOTECHNOLOGY)

antibodies to GADD153: (sc-575, SANTA CRUZ BIOTECHNOLOGY)

In short, an experiment was carried as follows.

For a tissue staining test, cultured cells were immobilized for 10 minutes at room temperature (RT) with 4% formaldehyde and incubated for 30 minutes with 1% bovine serum albumin (BSA). Antibodies to GRP78 and GADD153 were each used at a 1:200 dilution. For secondary antibodies, a 1:2000 dilution of Alexa Fluor® 488 labeling goat anti-mouse IgG (Life Technologies) was used. Cellular nuclei were then stained with DAPI (Vector Laboratories, Inc., Burlingame, Calif.). Slides were then observed with a fluorescent microscope (TCS SP2 AOBS; Leica Microsystems, Welzlar, Germany).

Western blot: Electrophoresis was applied to a protein extracted and obtained in a RIPA buffer with 7.5% polyacrylamide. The isolated protein was transferred onto a PVDF membrane (PALL LIFE SCIENCE (catalog number: EH-2222)). A Tris buffered saline (10 mM Tris-HCl, pH 7.4; 100 mM NaCl) (TBS-T) comprising 0.1% (vol/vol) polyethylene sorbitan monolaurate (Nacalai Tesque, catalog number: 28353-85) complemented with 5% NON FAT DRY MILK (CELL SIGNALING, catalog number: 9999) and a blotted membrane were incubated for 1 hour for a blocking operation. The membrane was immersed in anti-GRP78 antibodies diluted 1000 fold with TBS-T complemented with 5% NON FAT DRY MILK and reacted for 1 hour at room temperature. After washing three times with TBS-T and incubating with a mouse-IgG antibody HRP complex (CELL SIGNALING (catalog number: 7074P2)) and washing, a band illuminated with an ECL-ADVAVCE Western Blotting Detection Kit (GE Healthcare Japan (catalog number: RPN2135V)) was detected.

The following primary antibodies were used in the present technology.

Anti-GRP78 antibodies (SANTA CRUZ BIOTECHNOLOGY, SC-376768)

Anti-IRE1 antibodies (Cell Signaling Technology, 14C10)

Anti-GAPDH antibodies (MEDICAL & BIOLOGICAL LABORATORIES, M171-3)

The secondary antibodies were as follows.

HRP labeled anti-rabbit IgG or anti-rabbit IgG (Cell Signaling Technology) (1:5000 dilution)

The primary antibodies and secondary antibodies were both incubated. The membrane was exposed to light with an ECL Advance Western Blotting Detection Kit (GE Healthcare, Piscataway, N.J.) and then studied with an LAS4000S imaging system (Fuji Film, Tokyo)

(Cell Stimulation)

Cells were stimulated for 24 hours with 10 ng/ml TGFβ2 (R&D SYSTEMS). Further, cells stimulated for 24 hours with 10 μM of thapsigargin (TG; Alomone Laboratories Ltd., Jerusalem, Israel) were used as a positive control of ER stress.

(Results)

Figure 3:
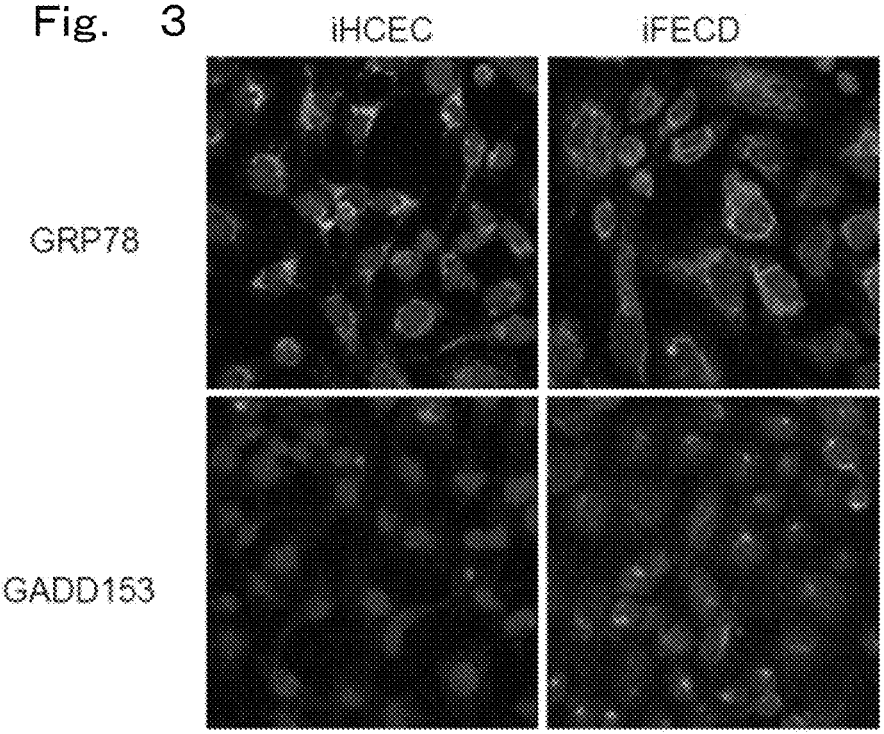
FIG. 3 is a result of immunostaining showing that endoplasmic reticulum stress on corneal endothelial cells is exacerbated in Fuchs' endothelial corneal dystrophy. It is shown that expression of endoplasmic reticulum stress associated proteins such as GRP78 and GADD153 is prominent in iFECD. In the top row, green fluorescence of GRP78 is sparsely observed in iHCEC of the left panel, while green fluorescence is prominently observed in iFECD of the right panel. On the other hand in the bottom row, green fluorescence of GADD153 is hardly observed in the left panel, while the green fluorescence is prominently observed in the right panel.

The results are shown in FIG. 3. Increase in expression of GRP78 and GADD153, which indicate increased endoplasmic reticulum stress, was observed in a Fuchs' endothelial corneal dystrophy model, relative to corneal endothelial cells from a normal cornea.

Example 3: TGF-β Promotes ER Stress in Corneal Endothelial Cells

In order to confirm that TGF-β promotes ER stress in corneal endothelial cells, a Western blot similar to Example 2 was performed and the tendency of GRP78 in addition to IRE1, which is a membrane protein involved in stress signaling on an endoplasmic reticulum membrane, was observed in the present Example. Cells were stimulated with 10 ng/ml TGFβ2 (R&D SYSTEMS). Further, cells stimulated with thapsigargin (TG; Alomone Laboratories Ltd., Jerusalem, Israel) were used as a positive control of ER stress.

(Materials and Methods)

Western blot was performed in accordance with the description in Example 2. The following antibodies were used in addition to those used in Example 2.
Antibodies to IRE1: (14C10, Cell Signaling Technology)
TGF-β2: (302-B2-002, R&D SYSTEMS)

(Results)

Figure 4:
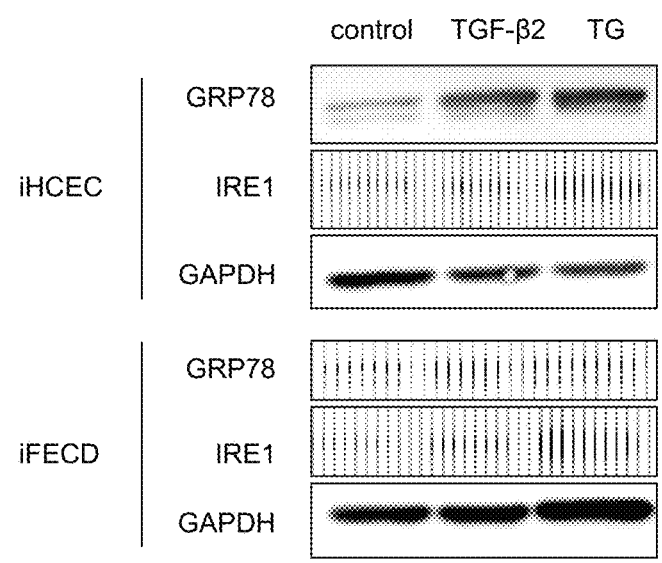
FIG. 4 is a diagram showing that TGF-β promotes ER stress on corneal endothelial cells. The top panel shows iHCEC and the bottom panel shows iFECD. Each panel shows, from the left side, a control (unstimulated), and stimulations with TGF-β or TG. Each panel shows, from the top, GRP78, IRE1 and GAPDH. It is shown that expression levels of the chaperone GRP78 and the stress sensor IRE1 are induced by TGFβ and the expression level thereof is elevated, particularly in iFECD. TG refers to thapsigargin, which was used as a positive control of ER stress.

The results are shown in FIG. 4. Expression of a chaperone GRP78 and stress sensor IRE1 was induced by TGFβ in Fuchs' endothelial corneal dystrophy model cells and normal cells. The expression level was high especially in Fuchs' endothelial corneal dystrophy model cells. TG refers to thapsigargin, which was used as a positive control of ER stress.

Example 4: Corneal Endothelial Cells with Fuchs' Endothelial Corneal Dystrophy are Highly Sensitive to Endoplasmic Reticulum Stress In the present Example, a TGFβ signal inhibitor SB431542 was administered to examine whether ER stress elevation is cancelled in order to show that corneal endothelial cells with Fuchs' endothelial corneal dystrophy are highly sensitive to endoplasmic reticulum stress.

(Materials and Methods)

SB431542 was obtained from TOCRIS (catalog number: 1614).

(Technology)

The human corneal endothelial cells (iHCEC) or corneal endothelial cells with Fuchs' endothelial corneal dystrophy (iFECD) prepared in the Preparation Examples were seeded on a culture dish coated with FNC Coating Mix and cultured for about 3 days until reaching sub-confluence under the condition of 5% $CO_2$ at 37° C. Furthermore, TGFβ2, SB431542 and TG were added and the cells were incubated for 24 hours under the condition of 5% $CO_2$ at 37° C. Cell morphology and apoptosis were then observed under a phase difference microscope.

(Results)

Figure 5:
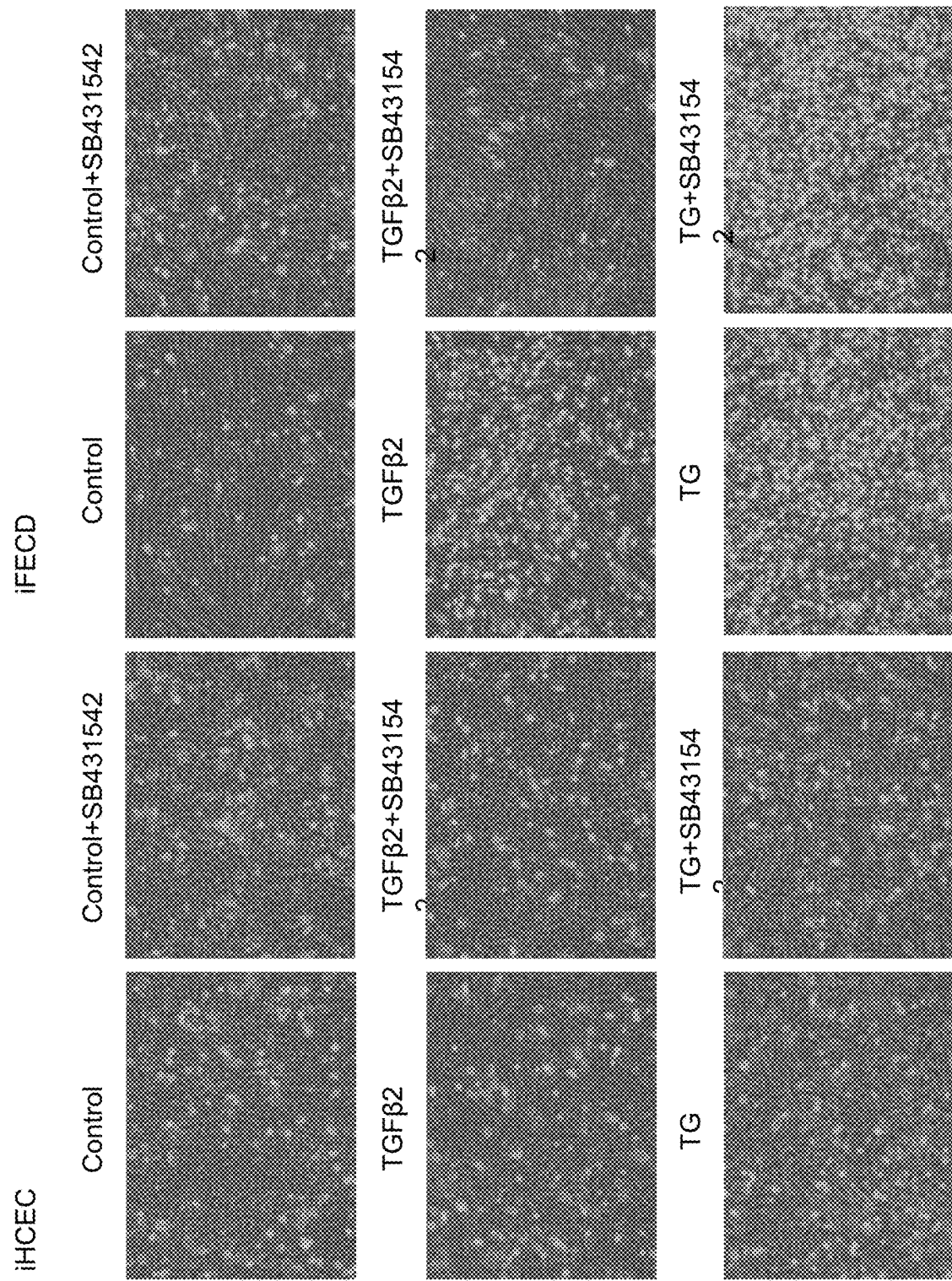
FIG. 5 is a result showing that corneal endothelial cells with Fuchs' endothelial corneal dystrophy have a higher level of endoplasmic reticulum stress relative to the control due to TGF beta (corneal endothelial cells with Fuchs' endothelial corneal dystrophy are highly sensitive to endoplasmic reticulum stress). The left side shows iHCEC and the right side shows iFECD. On each side, the top left shows the result for a control and the top right shows a result of adding SB431542 to the control, the middle left shows the result for a TGF-β2 stimulation and the middle right shows the result of adding SB431542 to the TGF-β2 stimulation. The bottom left shows the result of a TG stimulation and the bottom right shows the result of adding SB431542 to the TG stimulation.
Figure 6:
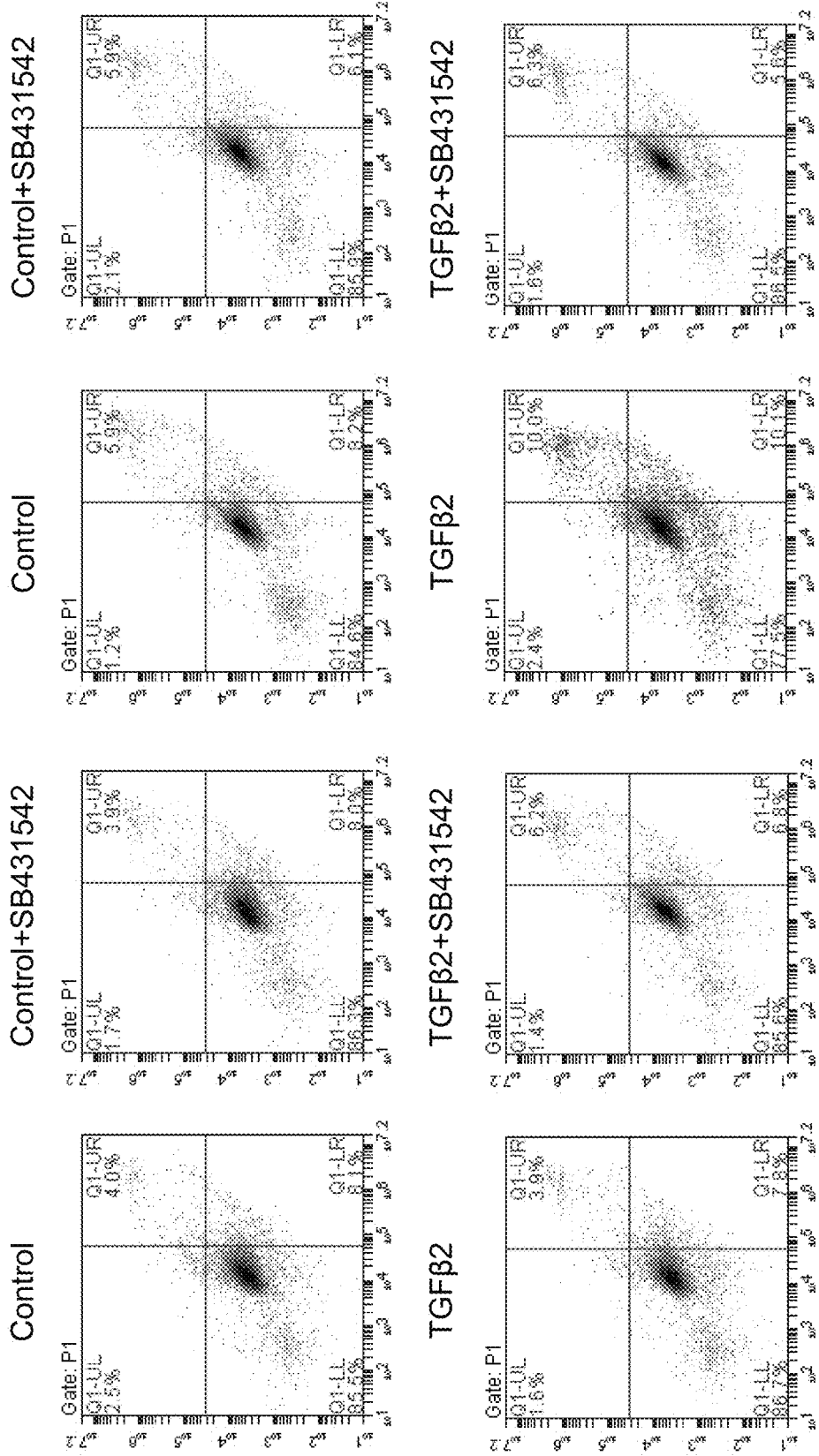
FIG. 6 is a result showing that corneal endothelial cells with Fuchs' endothelial corneal dystrophy have a higher level of endoplasmic reticulum stress relative to the control due to TGFβ (corneal endothelial cells with Fuchs' endothelial corneal dystrophy are highly sensitive to endoplasmic reticulum stress). This is a representative example of a result assessing apoptosis in the cells of FIG. 5 by flow cytometry. The left side shows iHCEC and the right side shows iFECD. On each side, the top left shows the result of a control and the top right shows the result of adding SB431542 to the control. The bottom left shows the result of a TGF-β2 stimulation and the bottom right shows the result of adding SB431542 to the TGF-β2 stimulation.
Figure 7:
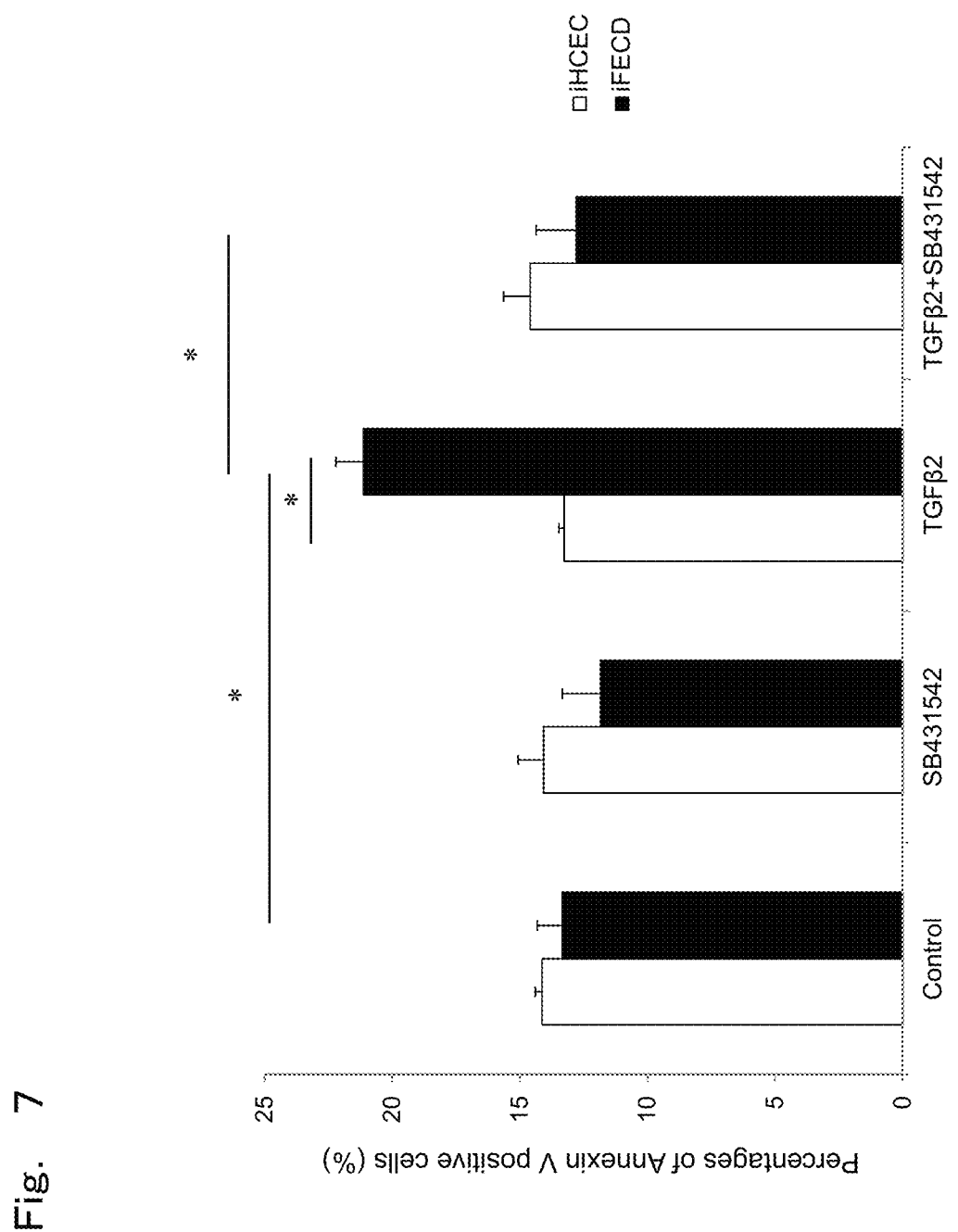
FIG. 7 is a graph showing that SB431542 suppresses apoptosis in Fuchs' endothelial corneal dystrophy. The y axis indicates the percentage of annexin V positive cells. The x axis indicates, from the left, the control, SB431542, TGFβ2, and TGFβ+SB431542. White indicates iHCEC and black indicates iFECD. * indicates statistical significance (p<0.01). The bar shows a standard deviation.

The results are shown in FIG. 5. Cells were damaged by TGFβ2 only in iFECD, and a large amount of floating cells was observed relative to iHCEC. Floating cells were cancelled with SB431542. Meanwhile, a large amount of floating cells were observed especially in iFECD due to TG. However, this was not cancelled with SB431542. This indicates that SB431542 is not a non-specific cell damage suppressant, but is specific to cell damage induced by a TGFβ signal. FIG. 6 shows a typical example of results of assessing apoptosis in cells of FIG. 5 by flow cytometry, and FIG. 7 shows a graph plotting annexin V positive apoptosis cells in the vertical axis.

(Materials and Methods)

Flow Cytometry:

The human corneal endothelial cells (iHCEC) or corneal endothelial cells with Fuchs' endothelial corneal dystrophy (iFECD) prepared in the Preparation Examples were seeded on a culture dish coated with FNC Coating Mix and culture for about 3 days until reaching sub-confluence under the condition of 5% $CO_2$ at 37° C. Furthermore, TGFβ2 and SB431542 were added and the cells were incubated for 24 hours under the condition of 5% $CO_2$ at 37° C. Cells were peeled off with ACCUMAX. Annexin V or PI positive cells were measured by using Annexin V and PI and a flow cytometer (FACS Aria II (BD Biosciences, Franklin Lakes, N.J.)) with MEBCYTO Apoptosis Kit (Annexin V-FITC Kit) 100 test (4700, MEDICAL & BIOLOGICAL LABORATORIES).

(Results)

The results are shown in FIG. 7. As shown, for Fuchs' endothelial corneal dystrophy cells, apoptotic cells increased due to TGFβ2 and the increase was cancelled by SB431542. It is suggested that apoptosis, which spontaneously occurs in Fuchs' endothelial corneal dystrophy, can be treated or its progression prevented by suppressing endoplasmic reticulum (ER) associated stress by inhibiting a TGFβ signal.

Example 7: TGFβ Signal Inhibitor Suppresses Apoptosis in Fuchs' Endothelial Corneal Dystrophy The present invention examined whether TGFβ signal inhibitors other than SB431542 (A-83-01, ALK5 inhibitors) can suppress apoptosis in Fuchs' endothelial corneal dystrophy. This was observed by counting annexin V positive cells used as an indicator of apoptosis in this Example.

(Technology)

The human corneal endothelial cells (iHCEC) or corneal endothelial cells with Fuchs' endothelial corneal dystrophy (iFECD) prepared in the Preparation Examples were seeded on a culture dish coated with FNC Coating Mix and culture for about 3 days until reaching sub-confluence under the condition of 5% $CO_2$ at 37° C. Furthermore, TGFβ2, SB431542 and TGFβ signal inhibitor A-83-01 (Wako, Osaka; catalog No: 018-22521), ALK5 inhibitor (Wako catalog No: 012-23021; CAS No. 446859-33-2; 2-(3-(6-methylpyridine-2-yl)-1H-pyrazole-4-yl)-1,5-naphthyridine) were added and the cells were incubated for 24 hours under the condition of 5% $CO_2$ at 37° C. The cells were peeled off with ACCUMAX. Annexin V or PI positive cells were measured by using annexin V and propidium iodide (PI) with a flow cytometer (FACS Aria II (BD Biosciences, Franklin Lakes, N.J.)).

(Results)

Figure 8:
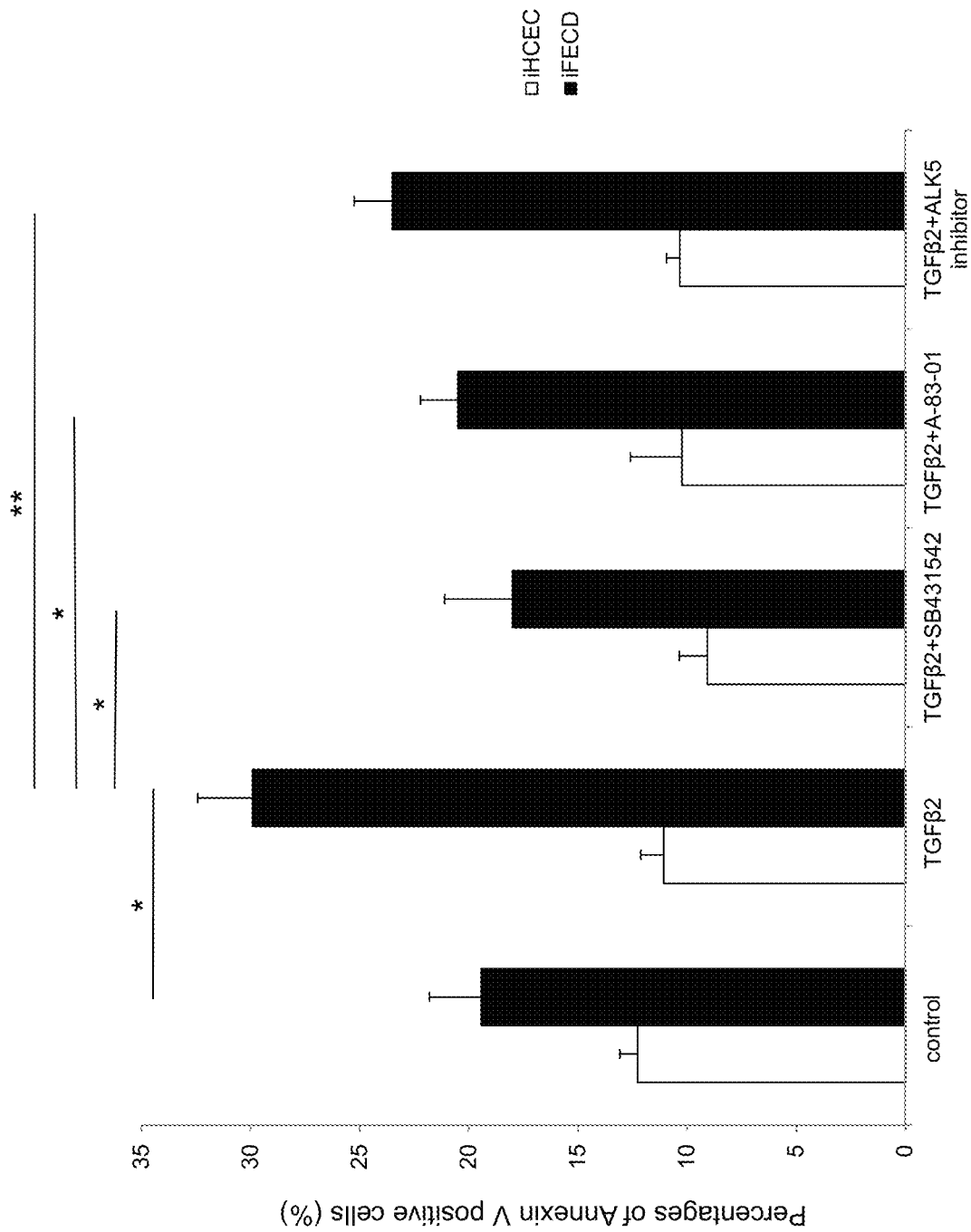
FIG. 8 shows a result of an experiment similar to FIG. 7 with A-83-01 and an ALK5 inhibitor. The y axis indicates the percentage of annexin V positive cells. The x axis indicates, from the left, the control, TGFβ2, TGFβ2+SB431542, TGFβ2+A-83-01, and TGFβ2+ALK5 inhibitor. White indicates iHCEC and black indicates iFECD. * indicates statistical significance (p<0.01). The bar shows a standard deviation.

The results are shown in FIG. 8. As in Example 6, apoptosis positive cells increased due to TGFβ2 and the increase was cancelled by SB431542 in Fuchs' endothelial corneal dystrophy cells. Furthermore, it was found that A-83-01 and ALK5 inhibitors, which are TGFβ signal inhibitors other than SB431542, suppress apoptotic cells.

It was demonstrated in view of the above that a disease, disorder or condition associated with endoplasmic reticulum (ER) of a corneal endothelium, especially apoptosis, can be treated or prevented by using not only SB431542, but also a TGFβ signal inhibitor.

Example 9: Experiment with Anti-IGF-β2 Antibody and Smad Inhibitor

An experiment similar to Example 8 can be conducted by using an anti-TGF-β2 antibody (R&D SYSTEMS; catalog No: AB-112-NA) and a Smad inhibitor (CALBIOCHEM; catalog No: 556405).

Example 10: ER Stress Promotion Due to TGF-β in Fuchs' Endothelial Corneal Dystrophy In the present Example, a Western blot was performed as in Example 2 to investigate the expression of the molecular chaperone GRP78 and CHOP involved with apoptosis due to an ER stress response in order to confirm that a stronger ER stress is elicited by TGF-β in Fuchs' endothelial corneal dystrophy. Further, expression of phosphorylated PERK and ATF6 involved in stress signaling on an endoplasmic reticulum membrane was also examined therewith. A stimulation was applied with 10 ng/ml of TGFβ2 (R&D SYSTEMS). The chronological change was also examined therewith.

(Materials and Methods)

Western blot was performed in accordance with the description of Example 2. The following antibodies were used in addition to those in Example 2.
Antibodies to PERK: (D11A8, Cell Signaling Technology)
Antibodies to phosphorylated PERK: (sc-32577, SANTA CRUZ BIOTECHNOLOGY)
Antibodies to ATF6: (73-505, Bio Academia)
Antibodies to GRP78: (SC-376768, SANTA CRUZ BIO-TECHNOLOGY)
Antibodies to CHOP: (L63F7, Cell Signaling Technology)
TGF-β2: (302-B2-002, R&D SYSTEMS)

(Results)

Figure 9:
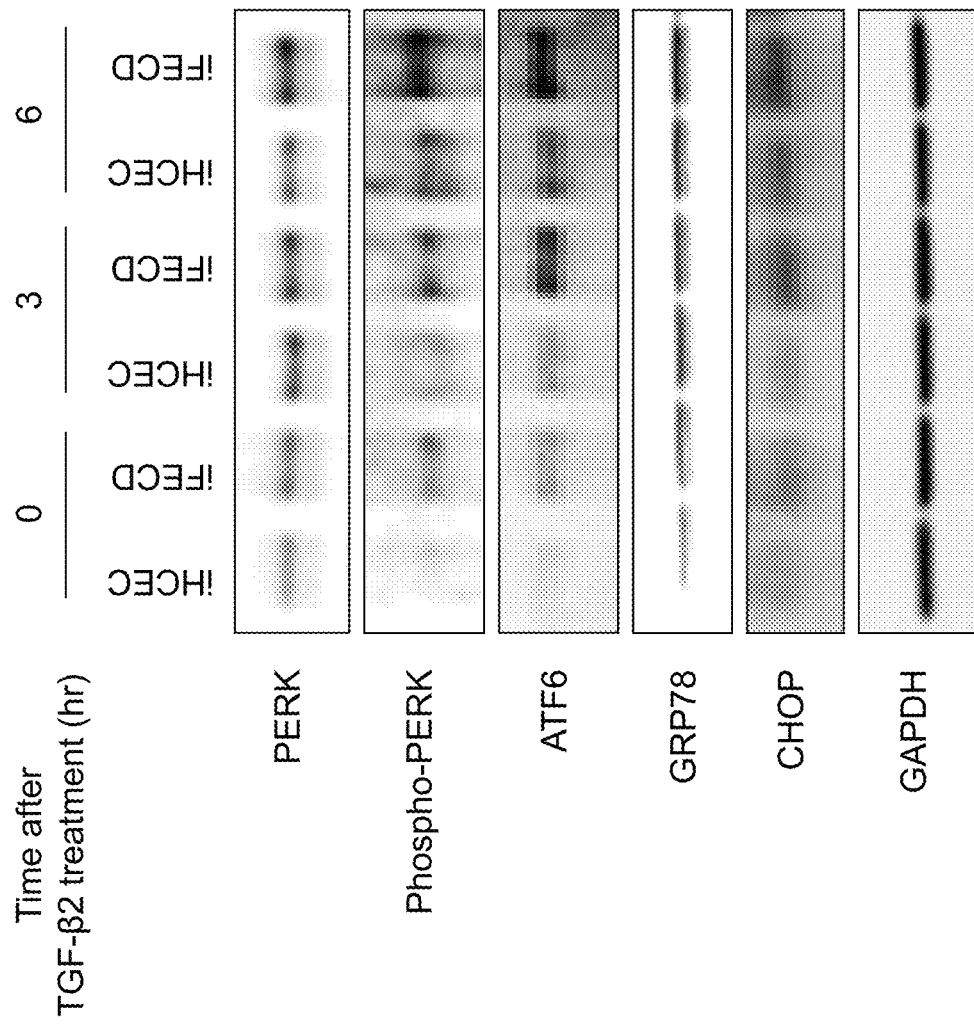
FIG. 9 is a diagram showing that TGF-β promotes ER stress in corneal endothelial cells. It is shown that ER stress is induced by TGF-β in iFECD. Results of western blot for different times after TGF-β2 treatment are shown 2 columns at a time (in each pair of 2 columns, the left column shows iHCEC and the right column shows iFECD), indicating, from the left, 0 hours, 3 hours, and 6 hours after treatment. From the top row, PERK, phosphorylated PERK, ATF6, GRP78, CHOP, and GAPDH are shown. PERK and ATF6 indicate ER stress sensors, GRP78 indicates a molecular chaperone responsible for ER integrity, and CHOP indicates an ER stress mediated apoptosis inducing factor. GAPDH is a control. It is shown that TGF-β promotes phosphorylation of an ER stress sensor PERK and promotes ATF6 expression. Further, expression of the chaperone GRP78 increases. Furthermore, it is shown that expression of CHOP increases and apoptosis is induced by ER stress.

The results are shown in FIG. 9. It was shown that TGF-β promotes phosphorylation of PERK, which is an ER stress sensor, and promotes expression of ATF6. Further, it was shown that expression of the chaperone GRP78 increases. More significant promotion of phosphorylation and promotion of expression was observed in iFECD relative to iHCEC. In this manner, it was shown that TGF-β increased an ER stress marker. Furthermore, it was shown that expression of CHOP increases and results in apoptosis due to ER stress. Further, it was shown that the increase is seen after 3 hours and the effect of the increase is enhanced after 6 hours.

Example 11: Involvement of Mitochondrial Failure in Corneal Endothelial Cells with Fuchs' Endothelial Corneal Dystrophy In the present Example an experiment was conducted to confirm that mitochondrial failure is involved in corneal endothelial cells with Fuchs' endothelial corneal dystrophy.

(Method)

As described in the aforementioned Preparation Examples, the inventors have established normal donor corneal HCEC (iHCEC) and immobilized cell model (iFECD) of human corneal endothelial cells (HCEC) of FECD patients, which were used in the present Example. The objective of the Example is to use a cell model to investigate the involvement of mitochondrial failure in FECD.

The mitochondrial membrane potential of iFECD and iHCEC was assessed with a JC-1 dye (BD Bioscience, 551302) and MitoTracker® Red CMXRos (Life Technologies, M-7512) in order to investigate the morphological change in mitochondria.

Release of cytochrome c from the mitochondria to cytoplasm was assessed by mitochondria fractionation with a Mitochondria Isolation Kit (Thermo SCIENTIFIC, 89874) and Western blot (Anti-Cytochrome C antibody, abcam, ab13575).

Caspase 9, caspase 3 and poly(ADP-ribose) polymerase (PARP) were assessed by Western blot in iHCEC stimulated with a mitochondrial stress stimulant staurosporine (abcam, ab120056) in order to assess the involvement of mitochondrial failure in apoptosis.

(Results and Discussion)

Figure 10:
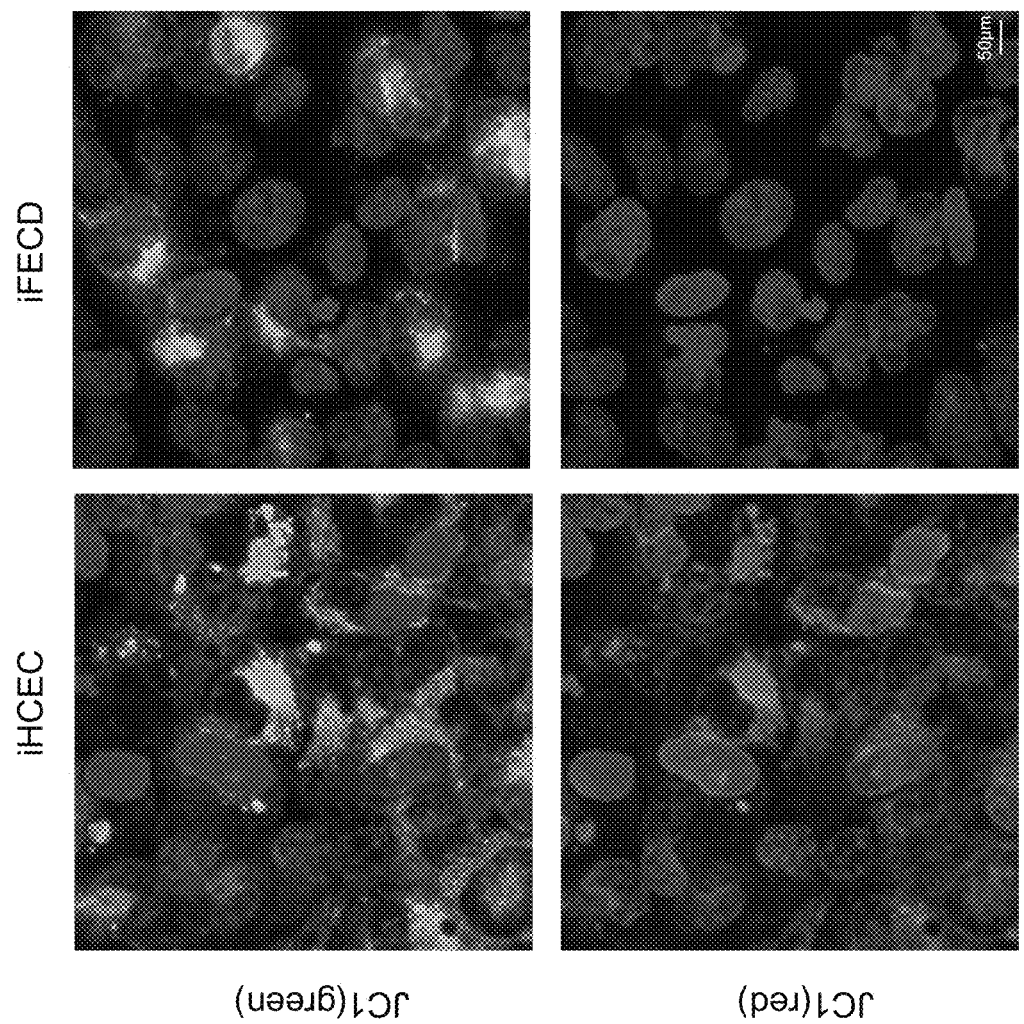
FIG. 10 is an image of staining with fluorescent dye JC-1 (5,5',6,6'-tetrachloro-1,1',3,3'-tetraethylbenzimidazolylcarbocyanine iodide). Mitochondrial depolarization is exhibited in iFECD. The left column shows iHCEC and the right column shows iFECD. The top row shows JC1 staining (stained in green) and the bottom row shows JC1 staining (stained in red). Green indicates mitochondria and red indicates mitochondrial membrane potential. Blue indicates DAPI (stains a nucleus). Decrease in mitochondrial membrane potential is observed in iFECD relative to iHCEC. For green staining indicating mitochondria (top section), green fluorescence indicating mitochondria is observed in both the left and right panels. For red staining indicating mitochondrial membrane potential (bottom section), red fluorescence is prominently observed in the left panel, but is barely observed in the right panel.
Figure 11:
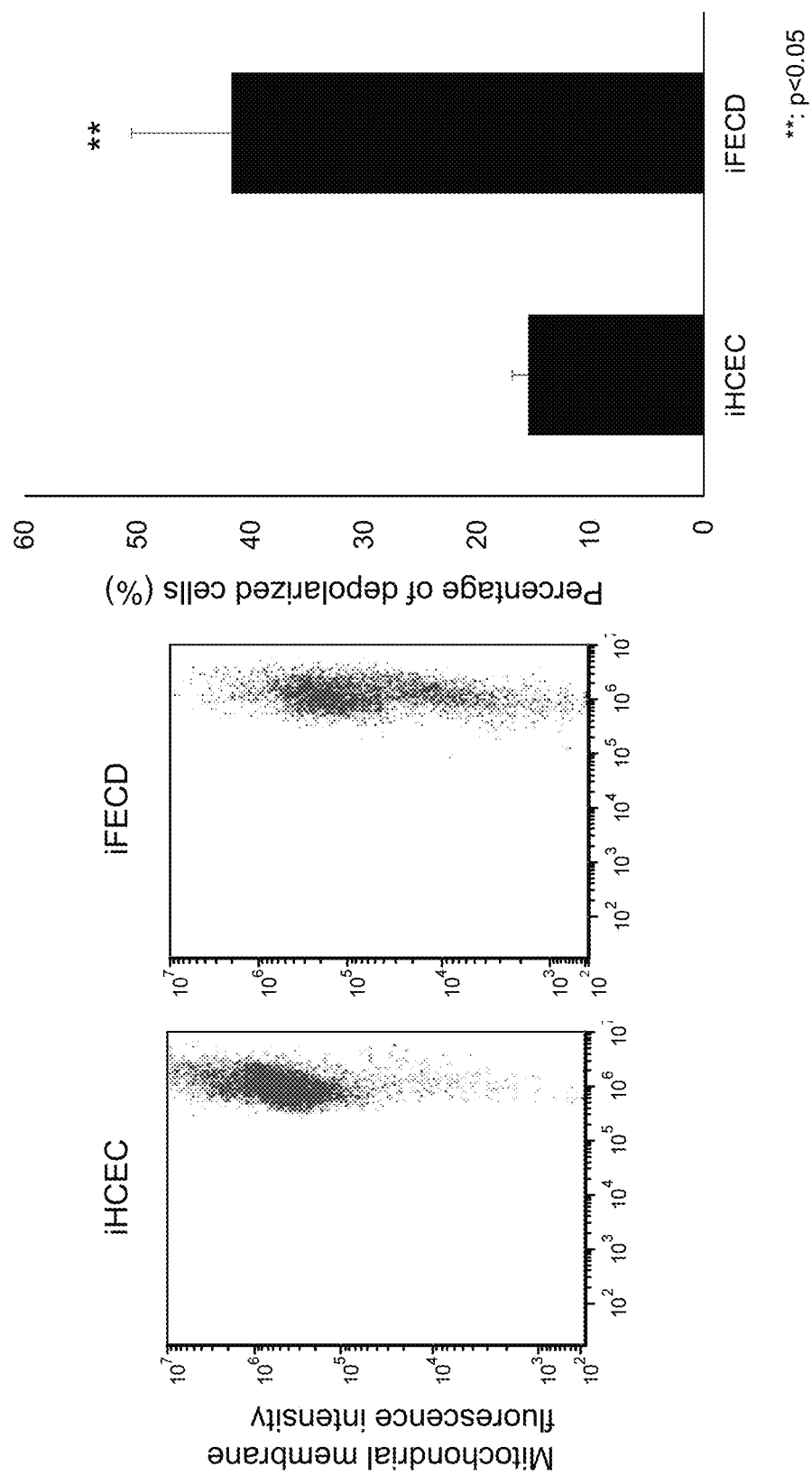
FIG. 11 shows mitochondrial membrane potential measured with MitoTracker® by using flow cytometry. Mitochondrial depolarization is exhibited in iFECD. The left panel shows fluorescence intensity of a mitochondrial membrane. The right panel shows iHCEC in the left graph and iFECD in the right graph. The left panel shows the percentage of depolarized cells. The left column shows iHCEC and the right column shows iFECD. The mitochondrial membrane potential is significantly decreased in iFECD relative to iHCEC. ** indicates statistical significance (p<0.05). The color of the left panel (green and red) indicates depolarized cells with decreased membrane potential with green and non-depolarized cells without decreased membrane potential with red.

FIG. 10 assesses mitochondrial membrane potential by using a fluorescent probe JC-1 dye. Green fluorescence indicates mitochondria and red fluorescence indicates mitochondrial membrane potential. Lack of red fluorescence indicates that mitochondrial membrane potential is depolarized. Red fluorescence was weaker in iFECD than in iHCEC. FIG. 11 assessed mitochondrial membrane potential by using flow cytometry. It was revealed from the assessments with JC-1 and MitoTracker® that mitochondrial membrane potential is lower in iFECD than in iHCEC (in each of FIGS. 10 and 11).

Figure 12:
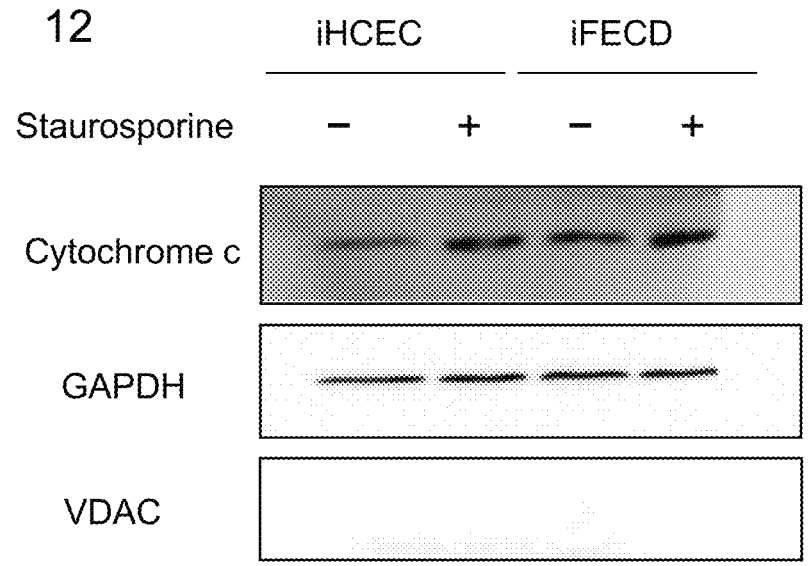
FIG. 12 shows cytochrome c leakage from mitochondria to cytoplasm. Cytochrome c leakage from mitochondria is measured here by Western blotting. More cytochrome c leakage is observed in iFECD than in iHCEC. Staurosporine is used as a control. The left two columns show iHCEC (left side indicates no staurosporine and the right side indicates the presence of staurosporine) and the right two columns show iFECD (left side indicates no staurosporine and the right side indicates the presence of staurosporine). From the top row, cytochrome c, GAPDH and VDAC staining are shown. GAPDH is a cytosol marker and VDAC is a mitochondria marker.

It was observed from Western blot that the level of cytochrome c in a mitochondrial fraction is higher in iFECD than in iHCEC (FIG. 12). Since leakage of cytochrome c from mitochondria to cytoplasm is observed in FIG. 12, it is shown that mitochondrial disorder has occurred in corneal endothelial cells with Fuchs' endothelial corneal dystrophy.

Example 12: Relationship Between Mitochondrial Disorder and Apoptosis

In the present example, a Western blot similar to Example 2 was performed to examine the expression of caspase 9, caspase 3, and PARP, which are proteins associated with apoptosis, as to whether a mitochondrial disorder in corneal endothelial cells lead to cell damage. A stimulation was applied with staurosporine to induce a mitochondrial disorder to examine the chronological change.

(Materials and Methods)

Western blot was performed in accordance with the descriptions in Example 2. The following antibodies were used in addition to those used in Example 2.
Antibodies to caspase 9: (9508S, Cell Signaling Technology)
Antibodies to caspase 3: (9662S, Cell Signaling Technology)
Antibodies to PARP: (9542S, Cell Signaling Technology)
Staurosporine: (ab120056, abcam)

(Results)

Figure 13:
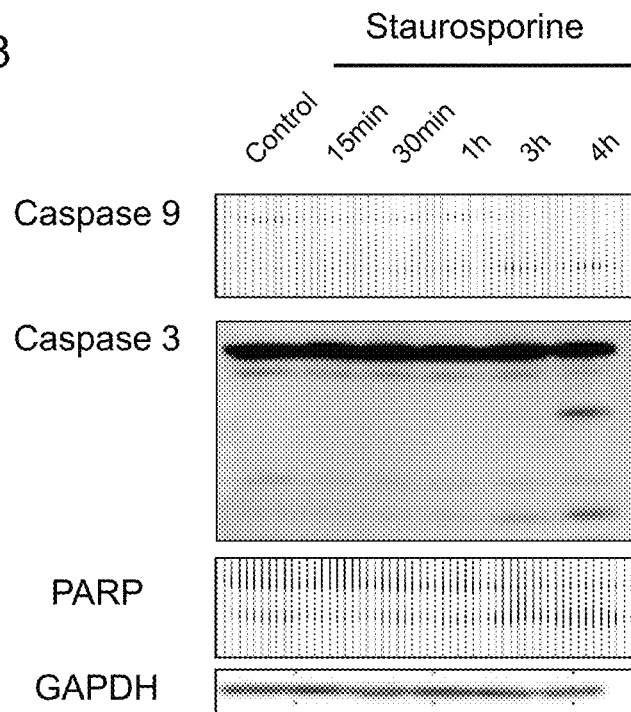
FIG. 13 shows involvement of mitochondrial failure in apoptosis. In this diagram, a mitochondrial disorder is induced with staurosporine and apoptosis associated proteins are measured by Wester blotting as to whether a mitochondrial disorder induces apoptosis. From the left column, the control, and 15 minutes, 30 minutes, 1 hour, 3 hours and 4 hours after a staurosporine stimulation are shown. From the top row, results of each of caspase 9, caspase 3, PARP and GADPH (control) are shown. Caspase 9, which is known to be activated by a mitochondrial disorder, can be seen to be activated and caspase 3 and PARP activation is also observed, demonstrating that apoptosis is induced by a mitochondrial disorder.

The results are shown in FIG. 13. FIG. 13 shows results of assessing downstream of signals by Western blot in iHCEC stimulated by a mitochondrial stress factor, staurosporine. A mitochondrial disorder was induced with staurosporine to activate caspase 9, caspase 3 and PARP. The morphology of mitochondria of iHCEC was normal, but expansion was observed in iFECD when observed with an electron microscope. Cells with decreased mitochondrial membrane potential were 11.7±1.7% in iHCEC, while it significantly increased to 41.9±10.2% in iFECD (p<0.05). Further, strong leakage of cytochrome c to cytoplasm was found in iFECD relative to iHCEC. In view of the results, mitochondrial stress induces leakage of cytochrome c, activation of caspase 9 known to be activated by a mitochondrial disorder is observed, and activation of caspase 3 and PARP is observed. Thus, it is understood that apoptosis is induced by a mitochondrial disorder. It is understood from the above that a mitochondrial disorder is involved in the pathology of FECD.

In view of the above, it is possible to assess from the present Example that mitochondrial failure is involved in the pathology of FECD and can be utilized as a target of a potent therapeutic agent. Since it is known that ER stress leads to a mitochondrial disorder in many cell species, it is understood that alleviation of ER stress with a drug can suppress a mitochondrial disorder and be applied in Fuchs' endothelial corneal dystrophy therapy.

Example 13: Denatured Protein Increases in Fuchs' Endothelial Corneal Dystrophy

The present Example shows that a denatured protein increases in Fuchs' endothelial corneal dystrophy.

In order to investigate accumulation of denatured proteins (also referred to as unfolded protein or incompletely folded protein) in a Fuchs' endothelial corneal dystrophy model, expression of an aggresome that is expressed in response to a denatured protein can be measured. It is known that proteins aggregated due to a denatured protein (or misfolded protein) or abnormality in protein degradation are ubiquitinated and accumulate near the centrosome by a dynein motor moving in microtubules to form an inclusion body called an aggresome.

In general, aggresomes are formed by a thermal shock, viral infection, oxidative stress or the like. In humans, there are reports of association thereof with diseases involving inclusion bodies in a cell such as Lewy bodies seen in nerve cells in Parkinson's disease, Mallory bodies seen in liver cells of alcoholic liver diseases, and glass-like bodies seen in astrocytes in amyotrophic lateral sclerosis.

(Materials and Methods)

It was confirmed by flow cytometry that aggresomes accumulated in Fuchs' endothelial corneal dystrophy.

(Equipment Used)

ProteoStat® Aggresome Detection Kit: (EZN-51035-K100, Enabling Discovery in Life Science®)

In short, the following was performed.

$1 \times 10^5$ human corneal endothelial cells (iHCEC) or corneal endothelial cells with Fuchs' endothelial corneal dystrophy (iFECD) were seeded onto a 6 well plate coated with an FNC Coating Mix and cultured for about 2 days until reaching sub-confluence under the condition of 5% $CO_2$ at 37° C. Furthermore, TGFβ2 (10 ng/ml; R&D SYSTEMS) was added and the cells were incubated for 24 hours under the condition of 5% $CO_2$ at 37° C. The cells were then peeled off with ACCUMAX™ (Funakoshi), and aggresomes were measured with a flow cytometer (FACS Aria II (BD Biosciences, Franklin Lakes, N.J.) by using a ProteoStat® Aggresome Detection Kit: (EZN-51035-K100, Enabling Discovery in Life Science®).

(Results)

The results are shown in FIG. 14. The fluorescence intensity of aggresomes was 1.22-fold and significantly higher in cells with Fuchs' endothelial corneal dystrophy (iFECD) relative to that in human corneal endothelial cells (iHCEC). Furthermore, aggresomes increased 1.11 fold by a TGF-β2 stimulation in Fuchs' endothelial corneal dystrophy and cell deaths were prominently observed.

It is shown in view of the above that there are many denatured proteins in the cells in Fuchs' endothelial corneal dystrophy and the amount thereof increases by a TGF-β signal. It is understood that endoplasmic reticulum stress due to denatured proteins is possibly related to the pathology of Fuchs' endothelial corneal dystrophy (FECD).

Example 13: Denatured Proteins (Unfolded Proteins) Accumulate in Fuchs' Endothelial Corneal Dystrophy The present Example shows that denatured proteins (unfolded proteins) accumulate in Fuchs' endothelial corneal dystrophy.

In order to investigate accumulation of denatured proteins in a Fuchs' endothelial corneal dystrophy model, expression of an aggresome that is expressed in response to a denatured protein can be measured. It is known that proteins aggregated due to a denatured protein (or misfolded protein) or abnormality in protein degradation are ubiquitinated and accumulate near the centrosome by a dynein motor moving in microtubules to form an inclusion body called an aggresome.

In general, aggresomes are formed by a thermal shock, viral infection, oxidative stress or the like. In humans, there are reports of association thereof with diseases involving inclusion bodies in a cell such as Lewy bodies seen in nerve cells in Parkinson's disease, Mallory bodies seen in liver cells of alcoholic liver diseases, and glass-like bodies seen in astrocytes in amyotrophic lateral sclerosis.

(Materials and Methods)

Cultured human corneal endothelial cells (iHCEC) or corneal endothelial cells with Fuchs' endothelial corneal dystrophy (iFECD) were seeded in a culture dish coated with an FNC Coating Mix and cultured for about 3 days until reaching sub-confluence under the condition of 5% $CO_2$ at 37° C. The cells were then peeled off with ACCUMAX™ (Funakoshi), and aggresomes were stained with a ProteoStat® Aggresome Detection Kit: (EZN-51035-K100, Enabling Discovery in Life Science®) and measured with a flow cytometer (FACS Aria II (BD Biosciences, Franklin Lakes, N.J.)

(Results)

The amount of expression of aggresomes is higher in iFECD relative to iHCEC. This can be interpreted as indicating that denatured proteins accumulate in a Fuchs' endothelial corneal dystrophy model.

The results of aggresomes and denatured proteins show that endoplasmic reticulum stress due to aggresomes and denatured proteins is involved in Fuchs' endothelial corneal dystrophy with regard to TGF-β signals.

Example 15: Diagnosis Using Aggresomes as an Indicator

The present Example demonstrates that diagnosis using aggresomes is possible. Aggresomes can be measured based on the descriptions in Examples 13-14 or the like.

A method of injecting a dye capable of staining aggresomes into an anterior chamber or the like can assess deposition of aggresomes in corneal endothelial cells for use in diagnosis.

Example 16: Preparation Example for Eye Drops

Preparation Example for Eye Drops

The composition of a tested substance at respective concentrations is shown below.

| | |
|---|---|
| SB431542 (available from TOCRIS etc.) | 0.1-30 mM, preferably 1-10 mM |
| Sodium chloride | 0.85 g |
| Sodium dihydrogen phosphate dihydrate | 0.1 g |
| Benzalkonium chloride | 0.005 g |
| Sodium hydroxide | appropriate amount |
| Purified water | appropriate amount |
| Total amount | 100 mg (pH 7.0). |

Eye drops can also be diluted with a base agent.
The composition of the base is as follows

| | |
|---|---|
| Sodium chloride | 0.85 g |
| Sodium dihydrogenphosphate dihydrate | 0.1 g |
| Benzalkonium chloride | 0.005 g |
| Sodium hydroxide | appropriate amount |
| Purified water | appropriate amount |
| Total amount | 100 mg (pH 7.0) |

As described above, the present invention is exemplified by the use of its preferred Embodiments. However, it is understood that the scope of the present invention should be interpreted solely based on the claims. It is also understood that any patent, any patent application, and any references cited in the present specification should be incorporated by reference in the present specification in the same manner as the contents are specifically described therein. The present application claims priority to Japanese Patent Application Nos. 2013-227048 and 2014-184172, whose content is incorporated herein by reference.

INDUSTRIAL APPLICABILITY

The present invention provides a technique available in industries (cell culture industry, pharmaceutical and the like) related to a therapeutic prophylactic drug for a disease, disorder or condition associated with ER stress in a corneal endothelium, especially a disease, disorder or condition associated with ER stress or apoptosis in Fuchs' endothelial corneal dystrophy, comprising a TGFβ-signal inhibitor.

The invention claimed is:
1. A method of treating Fuchs' endothelial corneal dystrophy (FECD) induced by transforming growth factor-β (TGF-β) induced endoplasmic reticulum (ER) stress in a corneal endothelium, said method comprising a step of administering an effective amount of a means for inhibiting TGF-β signal to a subject in need thereof that has the FECD, thereby treating the FECD in the subject.
2. The method of claim 1, wherein the disease, disorder or condition is associated with mitochondrial failure.
3. The method of claim 1, wherein the disease, disorder or condition is associated with apoptosis due to mitochondrial failure.
4. The method of claim 1, wherein the means for inhibiting TGF-β signal suppresses the disease, disorder or condition comprising a disorder of a corneal endothelial cell in Fuchs' endothelial corneal dystrophy.
5. The method of claim 1, wherein the means for inhibiting TGF-β signal suppresses at least one symptom of the FECD selected from the group consisting of decreased corneal endothelial density, guttae formation, hypertrophy of the Descemet's membrane, hypertrophy of a cornea, corneal epithelial disorder, turbidity in corneal stroma, photophobia, blurred vision, visual impairment, ophthalmalgia, epiphora, hyperemia, pain, bullous keratopathy, eye discomfort, diminished contrast, glare, and edema of the corneal stroma.
6. The method of claim 1, wherein the means for inhibiting TGF-β signal comprises 4-[4-(1,3-benzodioxole-5-yl)-5-(2-pyridinyl)-1H-imidazole-2-yl]benzamide, a pharmaceutical acceptable salt or solvate thereof, or a solvate of a pharmaceutically acceptable salt thereof.
7. The method of claim 1, further comprising administering an effective amount of a therapeutic agent selected from the group consisting of BiP inducer X (BIX), 4-phenyl butyric acid (PBA), trimethylamine N-oxide (TMAO), tauroursodeoxycholic acid (TUDCA), and teprenone for mitochondrial failure induced by ER stress to the subject.
8. The method of claim 1, wherein the corneal endothelium is from a primate.
9. The method of claim 1, wherein the corneal endothelium is from a human.
10. The method of claim 1, wherein the means for inhibiting TGF-β signal is administered in combination with an additional pharmaceutical ingredient.
11. The method of claim 1, wherein the means for inhibiting TGF-β signal is administered as eye drops.
12. The method of claim 1, wherein the means for inhibiting TGF-β signal comprises at least one of BMP-7, an anti-TGF-β antibody, or an anti-TGF-β receptor antibody.
13. The method of claim 1, wherein the means for inhibiting TGF-β signal comprises at least one of a siRNA of TGF-β, a siRNA of a TGF-β receptor, a shRNA of TGF-β, a shRNA of a TGF-β receptor, an aptamer of TGF-β, an aptamer of a TGF-β receptor or an antisense oligonucleotide of TGF-β.
14. The method of claim 1, wherein the means for inhibiting TGF-β signal comprises 6,7-dimethoxy-2-((2E)-3-(1-methyl-2-phenyl-1H-pyrrolo[2,3-b]pyridine-3-yl-prop-2-enoyl))-1,2,3,4-tetrahydroisoquinolone, a pharmaceutical acceptable salt or solvate thereof, or a solvate of a pharmaceutically acceptable salt thereof.
15. The method of claim 1, wherein the means for inhibiting TGF-β signal comprises 2-(3-(6-methylpyridine-2-yl)-1H-pyrazole-4-yl)-1,5-naphthyridine, a pharmaceutical acceptable salt or solvate thereof, or a solvate of a pharmaceutically acceptable salt thereof.
16. The method of claim 1, wherein the means for inhibiting TGF-β signal comprises 6-(4-(piperidine-1-yl)ethoxy)phenyl)-3-(pyridine-4-yl)pyrazolo[1,5-a]pyrimidine, a pharmaceutical acceptable salt or solvate thereof, or a solvate of a pharmaceutically acceptable salt thereof.
17. The method of claim 1, wherein the means for inhibiting TGF-β signal comprises 2-(5-chloro-2-fluorophenyl)-4-[(4-pyridinyl)amino]pteridine, a pharmaceutical acceptable salt or solvate thereof, or a solvate of a pharmaceutically acceptable salt thereof.
18. The method of claim 1, wherein the means for inhibiting TGF-β signal comprises 4-[3-(2-pyridinyl)-1H- pyrazole-4-yl]-quinoline, a pharmaceutical acceptable salt or solvate thereof, or a solvate of a pharmaceutically acceptable salt thereof.

19. The method of claim 1, wherein the means for inhibiting TGF-β signal comprises A-83-01 (3-(6-methyl-2-pyridinyl)-N-phenyl-4-(4-quinolinyl)-1H-pyrazole-1-carbothioamide), a pharmaceutical acceptable salt or solvate thereof, or a solvate of a pharmaceutically acceptable salt thereof.

* * * * *